United States Patent [19]

Johnston et al.

[11] 4,305,872

[45] Dec. 15, 1981

[54] POLYPEPTIDE DERIVATIVES

[75] Inventors: Robert B. Johnston; James L. Balk; John T. Pelton, all of Lincoln, Nebr.

[73] Assignee: Kenneth Wingrove, Minneapolis, Minn.

[21] Appl. No.: 86,417

[22] Filed: Oct. 19, 1979

[51] Int. Cl.$^3$ .................... C07C 103/52; A61K 37/00
[52] U.S. Cl. ...................... 260/112.5 R; 260/112.5 S; 260/112.5 TR; 260/112.5 LH; 424/177
[58] Field of Search ................ 260/112.5 R, 112.5 E, 260/112.5 T, 112.5 S, 112.5 LH, 112.5 TR; 424/177

[56] References Cited

U.S. PATENT DOCUMENTS 4,092,304 5/1978 Jones, Jr. et al. ............ 260/112.5 E
4,103,005 7/1978 Le .............................. 260/112.5 E

*Primary Examiner*—Delbert R. Phillips
*Assistant Examiner*—Blondel Hazel
*Attorney, Agent, or Firm*—William D. Stokes

[57] ABSTRACT

Compounds comprising polypeptide derivatives of the formula

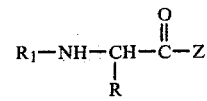

wherein $R_1$ is the amino acid sequence of the polypeptide minus the terminal amino acid; R is the side chain group determining the identity of the terminal amino acid; and Z is

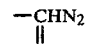

or $-CH_2X$ wherein X is Cl, Br, or I; are provided. Precursor peptides are peptide hypothalamic releasing and inhibitory factors, opiate peptides, and fragments thereof. The derivatives act as antagonists or agonists to the precursor peptides and are particularly useful in bioassay procedures.

14 Claims, 10 Drawing Figures

TRH-DMK INHIBITION STUDY

TRH-CMK STUDY

POLYPEPTIDE DERIVATIVES

BACKGROUND OF THE INVENTION

The pituitary gland, a very small gland that lies at the base of the brain, has been labeled the master gland of the human body. Physiologically, the pituitary is divided ino two distinct portions, the anterior pituitary and the posterior pituitary. Six life-controlling hormones, in addition to several less important hormones, are secreted by the anterior pituitary, while only two generally recognized important hormones are secreted by the posterior pituitary.

The principal hormones secreted by the anterior pituitary are: (1) Growth hormone, which promotes growth of the animal by effects on the metabolic functions throughout the body, especially protein formation; (2) Adrenocorticotropin which controls the secretion of the principal adrenocortical hormones, which hormones in turn affect the metabolism of glucose, proteins, and fats; (3) Thyroid-stimulating hormone controls the rate of secretion of thyroxine by the thyroid gland, and thyroxine in turn controls the rates of most chemical reactions in the entire body; (4) Prolactin promotes the development of the mammary glands and milk production; (5) Follicle-stimulating hormone; and (6) Luteinizing hormone. The latter two hormones control the growth of the gonads as well as their reproductive activities.

The two principal hormones secreted by the posterior pituitary are (1) Antiduretic hormone and (2) Oxytocin. The antiduretic hormone controls the rate of water excretion into the urine controlling thereby the water balance of the body tissue. Oxytocin performs two main functions, brings about delivery of milk from glands of the breast to the nipples during sucking and, it is believed, helps in the delivery of babies at the end of the gestation periods.

The anterior pituitary is a highly vascular gland with an extensive capillary system among its glandular cells and is directly connected to the hypothalamus of the brain by hypophyseal stalk through which the vascular system of the hypothalamus is directly connected with the vascular system of the anterior pituitary.

While it is well known that the hypothalamus produces releasing and inhibitory factors that control the secretions of the anterior pituitary, only recently has it become known that special neurons in the hypothalamus synthesize and secrete these releasing and inhibitory factors. The hypothalamic factors secreted are immediately absorbed into the vascular system of the hypothalamus flowing therethrough directly to the anterior pituitary gland. It is known that for each hormone synthesized by the anterior pituitary there is a corresponding hypothalamic releasing factor; and more important, for some of the anterior pituitary hormones, there is also a corresponding hypothalamic inhibitory factor. While the releasing factor is the most important factor for most of the anterior pituitary hormones, for prolactin, it is the hypothalamic inhibitory factor which exerts the important control.

The most important hypothalamic releasing and inhibitory factors corresponding to the anterior pituitary hormones described hereinabove are: (1) Thyroid-stimulating hormone releasing factor (TRH or TRF) which causes release of thyroid stimulating hormone; (2) Corticotropin releasing hormone (CRH or CRF) which causes release of adrenocorticotropin; (3) Growth (Somatotrophin) hormone releasing factor (GRH or GRF) which causes release of growth hormone; Growth (Somatostatin) hormone inhibiting factor (GIF or SRIF); (4) Luteinizing hormone releasing factor (LRH or LRF) which causes release of luteinizing hormone; (5) Follicle-stimulating hormone releasing factor (FRH or FRF) which causes release of follicle stimulating hormone; (6) Prolactin inhibitory factor (PIH or PIF) which causes inhibition of prolactin secretion; Prolactin release factor (PRF); and Melanocyte hormone release factor (MRH or MRF), Melanocyte inhibiting factor (MIH or MIF). For simplicity, the hypothalamic produced releasing and/or inhibitory agents will be referred to hereinafter by the initials TRF, CRF, GRF, GIF, LRF, FRF, PIF, PRF, MRF and MIF.

In addition to the aforementioned releasing and inhibitory factors, it is believed that an additional control on the anterior pituitary hormones is exerted by opiate peptides such as enkephalins or $\beta$-endorphin, which exercise their influence on the circulating levels of growth hormone, luteinizing hormone, and prolactin, particularly during sexual maturation. The opiate peptides are well-known for their property of exhibiting analgesic activity, presumably by acting at highly specific opiate receptor sites on the surface of certain neurons. Opiate peptides have been found principally in the brain, particularly in the cells of the limbic system which is associated with the arousal of emotion in humans and with smelling in lower vertebrates. It has been postulated that opiate peptide receptors in this area may be responsible for the euphoria-producing characteristics of the opiate drugs.

While the mechanism by which the opiate peptides regulate the anterior pituitary hormones is not entirely clear, it is believed that these peptides exert their influence by acting at certain receptor sites in the central nervous system to indirectly stimulate or inhibit release of anterior pituitary hormones. The hypothalamic releasing and inhibitory factors, however, appear to be released by hypothalamic neurons in response to appropriate stimuli, and are transported to specific receptor sites in the pituitary gland which interact with the specific factor to evoke the appropriate biological response.

The hypothalamic releasing and inhibitory factors and opiate polypeptides relevant to the invention are carboxyl terminal polypeptides.

The naturally occurring thyroid-stimulating hormone releasing factor (TRF) is the tripeptide L-pyroglutamyl-L-histidyl-L-prolinamide. Methods of synthesizing the compound are well-known. The structure of this compound is:

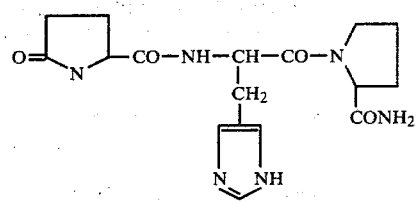

The secretion of TSH by the pituitary gland is normally regulated by an interaction between TRF, which stimulates TSH release, and thyroid hormones which inhibit it. TRF is a useful diagnostic compound for testing pituitary TSH reserve and for distinguishing pituitary from hypothalamic hypothyroidism (forms of thyroid malfunction). The TSH pattern of response to the administration of TRF may also be useful for studying thyroid function. Patients with hyperthyroidism (increased thyroid gland activity) or patients given T3 do not respond to TRF. Patients with primary hypothyroidism due to thyroid disease (high TSH) show exaggerated and prolonged response to TRF. Patients with pituitary hypothyroidism (secondary hypothyroidism) with low TSH levels fail to show a rise in plasma TSH after TRF administration. Patients with tertiary hypothyroidism due to hypothalamic disease show response to TRF.

The physiological influence of TRF on the reproductive behavior in mammal is well-documented, for example, administration of TRF in a therapeutically effective dosage prevents ovulation and subsequent elevation of serum progesterone. It is also known that administration of TRF, or certain pathological conditions which bring about an increased secretion or release of TRF by the hypothalamus also causes a marked increase in serum prolactin in mammals. It was subsequently discovered that an increase in TRF inhibits the secretion of the prolactin inhibitory factor (PIF) and there is now evidence that alterations in pituitary function are involved in tumor regression promoted by progesterone. Further, since TRF has been found in parts of the brain other than the hypothalamus and in other tissues such as intestine, it has been suggested that TRF may function as a neuro-secretory substance as well as a hormone releasing factor.

The luteinizing hormone releasing factor (LRF) has the established chemical decapeptide structure:

Pyroglu-His-Trp-Ser-Tyr-Gly-Leu-Arg-Pro-Gly-NH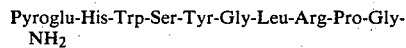

There is strong controversy concerning whether or not there is actually a follicle releasing hormone separable from luteinizing releasing factor. Since LRF promotes release of follicle stimulating hormone (FSH), it is also known as FSH-RH/LH-RH. Analogs of the decapeptide have been prepared, some of which behave as LRF and others as LRF antagonist, however, no one molecule has been shown to promote a selective release of only one of the gonadotropins. LRH does promote LH synthesis and can elevate total LH content of the pituitary gland. Under physiological conditions the luteinizing, growth, and prolactin hormones are subjected to primarily negative feedback control involving the gonado steroids which depends upon the release of particular hormones and positive control from the hypothalamus.

The chemical structure of the growth hormone inhibitory factor (GIF) is a tetradecapeptide containing 14 amino acids and a disulfide bond with the following structure:

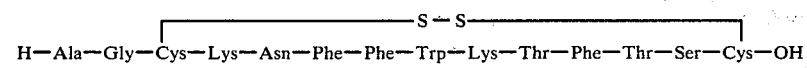

Somatotrophic or growth hormone (GH) affects virtually every cell in the body and is released in response to quite a few body stimuli including stress. GRF is highly effective for bringing about the release of GH from the pituitary and elevations of GH in the plasma, while GIF reduces the generation of cyclic adenosine 3′,5′monophosphate (cAMP) and blocks responses to agents which raise cAMP concentrations. In addition, GIF has been identified in many parts of the brain and influences behavior, inhibits release of TRF and blocks responses to TRF, inhibits secretion of prolactin and exerts a direct influence on both α and B cells of the pancreatic islets.

The control of prolactin secretion is predominantly inhibitory through the action of PIF, a small acid-soluble peptide. For the most part, prolactin-releasing activity is attributed to TRH. The neurotransmitter, dopamine, increases PIH activity in the portal blood of rats and decreases the release of prolactin. While other hormones, e.g. growth hormone, insulin, estrogen, and corticosteroid are also influential, prolactin is involved in the initiation and maintenance of lactation.

The chemical structure proposed for melanocyte hormone releasing factor (MRF) is a pentapeptide structure while the melanocyte inhibiting factor (MIF) is a tripeptide. MIF and some of its analogs have been reported to be active in inhibiting the oxotremorine-induced tremors which are believed to be similar in nature to those found in Parkinson's disease.

Two of the important opiate peptides are methionine enkephalin and leucine enkephalin, of the following respective structures:

(1) Tyr-Gly-Gly-Phe-Met
(2) Tyr-Gly-Gly-Phe-Leu

Thus, in view of the multifaceted activity of the peptide hypothalamic releasing and inhibitory factors, and the opiate peptides, particularly the activity of these peptides as affecting the inhibition, release, or circulating levels of the anterior pituitary hormones, it is highly desirable to provide pituitary modulator compounds by which the activity of the releasing and inhibitory factors or opiate peptides may be regulated. Modulator compounds, acting as agonists or antagonists to the several hypothalamic factors or opiate peptides, are thus useful to modify the various effects of the anterior pituitary hormones.

SUMMARY OF THE INVENTION

Accordingly, the invention provides biologically-active derivatives of peptide hypothalamic releasing and inhibitory factors and enkephalin opiate peptides and fragments thereof which act as pituitary modulators by exerting inhibitory or enhancing influence at pituitary receptor sites, for the releasing and inhibitory factors, or by indirect regulation, or by regulation of the circulating anterior pituitary hormones. In addition, the biologically-active derivatives of the opiate peptides act as opiate agonists or antagonists. The biologically-active derivatives of the invention thus function to modulate both neurological and endocrine processes, and link the neurological and endocrine systems.

DETAILED DESCRIPTION OF THE INVENTION

Figure 1:
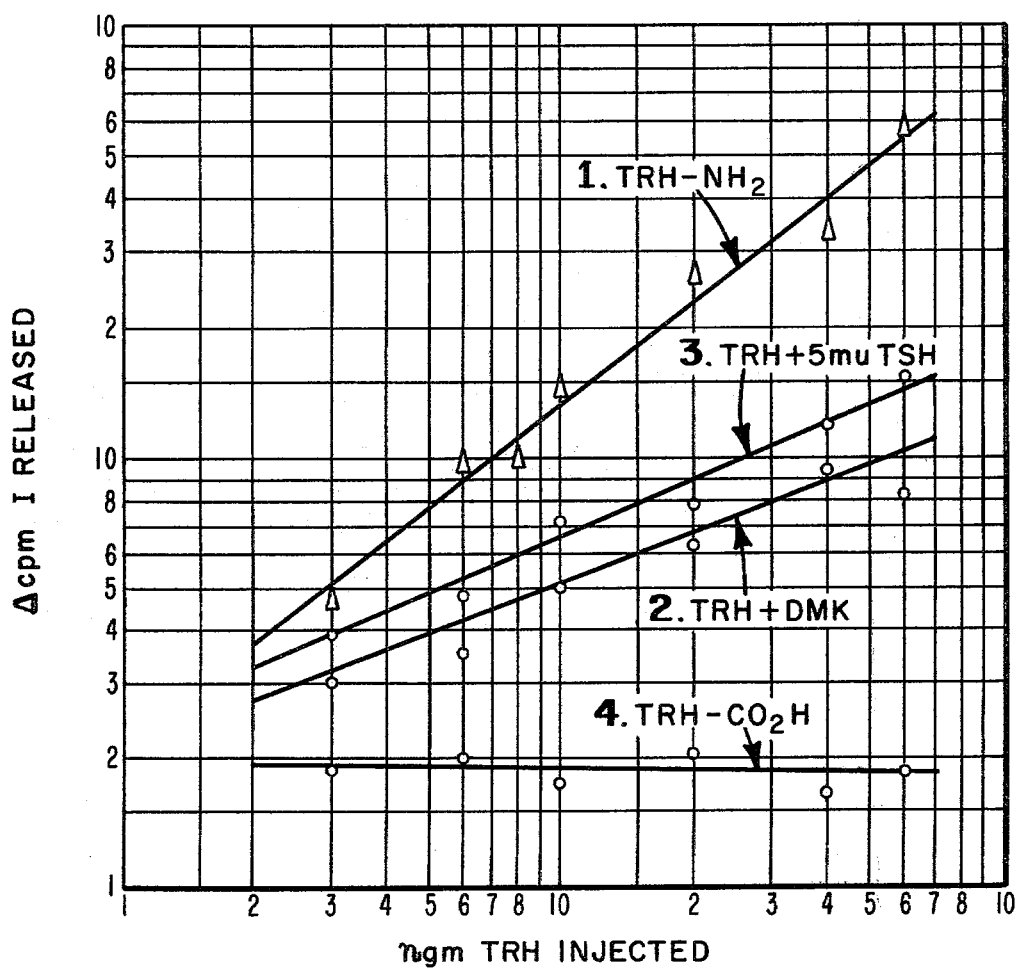
FIG. 1 is a graphic evaluation of a TRH-DMK bioassay.

The biologically-active derivatives of the invention comprise halomethylketone (HMK) or diazomethylketone (DMK) derivatives of a precursor carboxyl-terminal polypeptide selected from the group consisting of (a) polypeptide hypothalamic releasing factors; (b) polypeptide hypothalamic inhibitory factors; (c) enkephalin polypeptides; and (d) fragments thereof each consisting of a biologically-active polypeptide segment of one of said hypothalamic or enkephalin polypeptides. The precursor polypeptides are characterized by a sequence of $\alpha$-amino acid residues terminated at one end thereof with a terminal carboxyl group, and at the other end thereof with a terminal amino group; in the derivative of the invention, the hydroxyl group of the terminal carboxyl group is replaced by the group—$CHN_2$ or —$CH_2X$, wherein X is Cl, Br, or I.

While certain of the precursor polypeptides actually occur naturally with a terminal carboxamide group, for the purposes of this description the precursor polypeptides will be assumed to be in the form of their free acid. TRF, for example, is by convention described as pyroglu-His-Pro. The structure given supra, however, shows that the carboxylterminal $\alpha$-amino acid residue proline is present as prolinamide, and further, that the N-terminal amino acid residue, glutamic acid, is cyclized to form the cyclic amido group pyroglutamyl. Similarly, in LRF, the carboxyl-terminal $\alpha$-amino acid residue glycine is present as glycinamide. In these and similar instances, the free acid form of the precursor is synthesized.

As is well-known in the art, the $\alpha$-amino acid residues of the subject polypeptides are differentiated by their side-chain groups, so that the $\alpha$-amino acid sequences of the precursor peptides of this invention are conveniently described as:

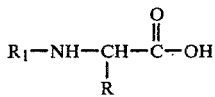

wherein $R_1$ is the $\alpha$-amino acid sequence minus the carboxyl-terminal $\alpha$-amino acid, and R is the side chain group which determines the identity of the carboxyl-terminal $\alpha$-amino acid. In the interest of accuracy and simplicity, the present description defines R as a particular $\alpha$-amino acid side chain group corresponding to the side chain of the carboxyl-terminal $\alpha$-amino acid. Thus, in the above formula, if the carboxyl-terminal amino acid is Pro, R is characterized as "Pro side chain". The identity of these side chains is well-known, and conveniently determined by referral to a text book of biochemistry, such as *Biochemistry: The Chemical Reactions of Living Cells*, Metzler, David E., (Academic Press, 1977).

DMK and HMK derivatives of the exemplary naturally-occurring polypeptide precursors TRF, LRF, and leucine and methoionine enkephalin are are accordingly given in Formula I, wherein X is Cl, Br, or I; R is Pro side chain where $R_1$ is pyroGlu-His; R is Met or Leu side chain when $R_1$ is Tyr-Gly-Gly-Phe; and R is Gly side chain when $R_1$ is PyroGlu-His-Trp-Ser-Tyr-Gly-Leu-Arg-Pro:

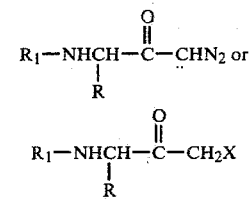

The derivatives of the invention further include DMK and HMK derivatives of the precursor polypeptides wherein one or more of the $\alpha$-amino acid residues of the peptide chain is an unnatural $\alpha$-amino acid, i.e., one which does not naturally occur at that position in the precursor peptide sequence, including $\alpha$-amino acids or isomers thereof which do not occur in nature. The unnatural $\alpha$-amino acid residue consists of an $\alpha$-amino acid residue wherein the side chain thereof has one more or one less atom, other than hydrogen, than the corresponding side chain of the natural $\alpha$-amino acid residue, or has the same number of atoms, other than hydrogen, as the corresponding side chain, but at least one is an atom of a different element than occurs in the side chain of the natural amino acid residue.

Exemplary of derivatives in this category are DMK and HMK derivatives of leucine-enkephalin or methionine-enkephalin, wherein either of the glycine amino acid residues in the peptide chain is replaced by alanine; i.e., the side chain of the glycine, consisting of hydrogen, is replaced by methyl, having one more atom other than hydrogen than the side chain of glycine, to form alanine. The structure of these derivatives are of the Formula II, wherein X is Cl, Br or I, R is Met side chain or Leu side chain and $R_1$ is Tyr-L-Ala-Gly-Phe or Tyr-Gly-L-Ala-Phe:

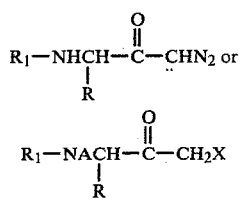

The DMK and HMK derivatives of the invention further include those derivatives of the precursor peptides wherein one or more of the $\alpha$-amino acid residues of the peptide chain is replaced with its stereoisomer. The stereoisomer may replace a naturally-occurring $\alpha$-amino acid residue, or a naturally-occurring amino acid residue which has been modified as exemplified in Formula II.

Exemplary of derivatives in this category are the DMK and HMK derivatives of leucine-enkephalin or methionine-enkephalin described in Formula II, wherein the L-alanine residue is replaced by D-alanine. The structure of these derivatives is set forth in Formula III, wherein X is Cl, Br, or I, R is Met side chain or Leu side chain and $R_1$ is Tyr-D-Ala-Gly-Phe or Tyr-Gly-D-Ala-Phe:

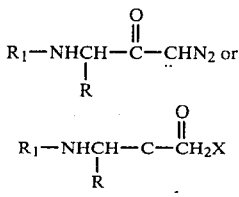

The derivatives of the invention additionally include DMK and HMK derivatives of the precursor polypeptides wherein at least one of the α-amino acid residues has been substituted with a methyl, ethyl or allyl group; this substitution may be made on the naturally-occurring α-amino acid residue, or on a residue modified as exemplified in Formulae II and III. The structure of exemplary derivatives wherein an α-amino acid residue has been methylated, ethylated, or allylated is given in Formula IV, wherein X is Cl, Br, or I, R is Pro side chain, and $R_1$ is pyroGlu-$N^{Im}$-methylHis or pyroGlu-$N^{Im}$-ethylHis:

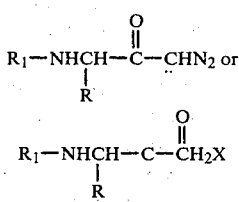

In these formulae, the histidine imidazole group of TRF has been methylated or ethylated.

The derivatives of the invention additionally include DMK and HMK derivatives of the precursor polypeptides wherein one or more of the naturally occurring α-amino acid residues or modified α-amino acid residues as exemplified in Formulae II, III or IV, includes a side chain having a ring structure, and this ring structure is modified by the addition or subtraction of one of the ring atoms thereof, and/or by the replacement of one or more of the ring atoms by an atom of a different element. The structure of exemplary derivatives wherein the ring structure is modified by the addition of a ring atom to the original structure and two of the original ring atoms are replaced by an atom of a different element is given in Formula V, wherein X is Cl, Br, or I, R is Pro side chain, and $R_1$ is pyroGlu-Phe:

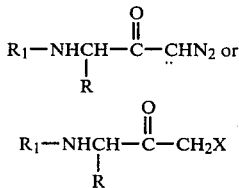

In these formulae, the two nitrogen atoms of the histidine imidazle ring of TRF are replaced by carbon, and the 5-membered imidazole ring has been expanded to a six-membered ring.

The DMK and HMK derivatives of the invention also include derivatives of the type set forth in Formulae II, III, IV and V wherein the precursor polypeptide, is a biologically-active fragment of a naturally-occurring polypeptide comprising a naturally-occurring hypothalamic inhibitory or releasing factor or enkephalin polypeptide wherein the terminal carboxyl α-amino acid residue has been deleted so that the penultimate α-amino acid residue of the naturally-occurring peptide becomes the carboxyl terminal amino acid residue. Exemplary of such precursor polypeptides are those of the Formula VI, wherein X is Cl, Br, or I; R is His side chain; and $R_1$ is pyroGlu; and of the Formula VII, wherein X is Cl, Br, or I; R is Pro side chain; and $R_1$ is pyroGlu-His-Trp-Ser-Tyr-D-Ala-Leu-Arg:

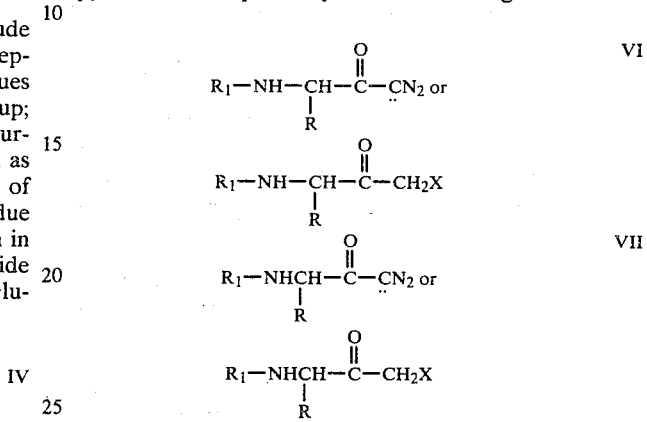

In Formula VI, the fragment consists of TRF wherein the terminal carboxyl α-amino acid residue proline is deleted so that the terminal carboxyl α-amino acid residue is histidine, and in Formula VII, the fragment consists of LRF wherein the terminal carboxyl α-amino acid residue glycine is deleted so that the terminal carboxyl α-amino acid residue is proline. Similarly, referring to Formula I, a precursor polypeptide fragment within the scope of the invention includes Tyr-Gly-Gly-Phe, comprising either leucine-enkephalin or methionine-enkephalin wherein the terminal α-amino acid residue methionine or leucine has been deleted so that the terminal carboxyl α-amino acid residue of the fragment is phenylalanine.

The α-amino acid residues of the biologically-active fragments of the invention can also be modified as exemplified by the Formulae II-V. For example, the fragment pyroGly-His of the Formula VI may be modified in the same way as the peptides of the Formula V, replacing the nitrogen atoms of the imidazole ring with carbon and expanding the 5-membered ring to a 6-membered ring to provide derivatives of the formula VIII, wherein X is Cl, Br, or I, R is Phe side chain, and $R_1$ is pyroGlu:

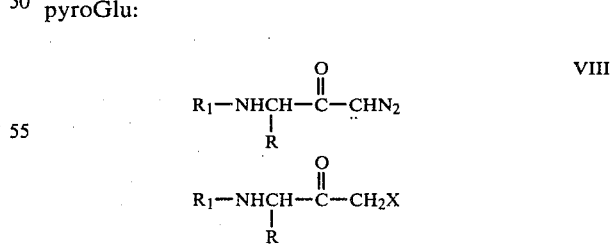

Further, the α-amino acid residues of the biologically-active fragments of the invention can also be modified as described supra by altering the side chain ring structure of a naturally-occurring α-amino acid residue by replacing one or more of the original ring atoms with an atom of a different element. For example, the fragment pyroGlu-His of Formula VI can be modified by replacing the nitrogen atom of the pyroglutamyl residue with a carbon atom (i.e., replacing pyroglutamic acid with cyclopentane carboxylic acid) to give a derivative of the Formula IX, wherein X is Cl, Br, or I, R is His, and $R_1$ is cyclopentoyl:

$$R_1-NHCHC-CHN_2 \quad \text{IX}$$
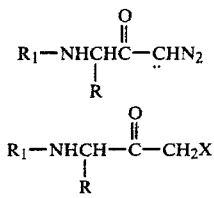

$$R_1-NHCH-\overset{O}{\underset{R}{\overset{\|}{C}}}-CH_2X$$

The derivatives of the invention are synthesized conveniently from synthetic hypothalamic releasing or inhibitory factors or enkephalins in the form of their free acids, which are in some cases available commercially. Otherwise, the precursor peptides may be synthesized by known methods, generally by activation of the α-amino acid acyl group and subsequent reaction with an α-amino acid amino group to form a peptide bond.

The general methods employed for the synthesis of the diazomethyl ketone derivatives of the present invention are by activation of the acyl group of the carboxyl terminal amino acid of the precursor peptide, for example with chloroformate, phosphorous pentachloride or perchlorophenol, with subsequent reaction of the activated peptide with diazomethane in the presence of a tertiary amine, according to the following reaction schemes:

$$R_1-NHCHCOOH + PCl_5 \longrightarrow R_1NHCHCCl + HCl$$

$$R_1NHCHCCl + CH_2N_2 \xrightarrow{R_3R_4R_5N}$$

$$R_1-NH-CH-\overset{O}{\overset{\|}{C}}-CHNH_2 + HCl,$$

wherein R is the carboxyl terminal amino acid side chain, $R_1$ is the α-amino acid sequence of a peptide minus the carboxyl terminal amino acid, and $R_3$-$R_5$ are alkyl groups of the tertiary amine. Alternatively, $$R_6-O-\overset{O}{\overset{\|}{C}}-Cl,$$

wherein $R_6$ is alkyl, or $C_6Cl_5$-OH, instead of $PCL_5$, are reacted similarly with $$R_1-NH-\overset{R}{\underset{}{CH}}-COOH,$$

followed by reaction with $CH_2N_2$ in the presence of $R_3R_4R_5N$ to form the corresponding diazomethyl ketone.

The halomethyl ketones are conveniently prepared by reaction of the diazomethylketone with anhydrous hydrohalic acid in an organic solvent, for example:

$$R_1-NH-\overset{R}{\underset{}{CH}}-\overset{O}{\overset{\|}{C}}-CHN_2 + HX \xrightarrow{\text{Dioxane}}_{\text{Ether}}$$

-continued
$$R_1-NH-\overset{O}{\overset{\|}{CHCCH_2X}} + N_2$$
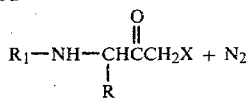

wherein X is Cl, Br, or I.

Advantageously, peptide intermediates, which are generally stable and usually crystallized, are used as starting materials; the intermediates are either available commercially, or can be synthesized by classical methods. For example, TRF in the form of the free acid can be synthesized from the dipeptide intermediate, pyroglutamyl histidine, which is obtained from pyroglutamyl histidine methyl ester by saponification of the ester to yield the free acid. Treatment of the intermediate free acid with dicyclohexylamine in a suitable solvent such as methanol forms the dicyclohexylamine salt; this amine salt of the intermediate is then reacted with proline methylester hydrochloride in DMF and DCCI (dimethylformamide and N,N-dicyclohexyl-carbodiimide) to form the TRF methylester, which is then saponified to the TRF free acid. The TRF free acid is then activated as described with, for example, ethylchloroformate, and the activated TRF reacted with diazomethane in a solvent such as anhydrous ethyl ether and in the presence of a tertiary amine such as a tri (lower alkyl) amine, e.g., triethylamine, to form the diazomethylketone derivative of the present invention. The halomethyl ketone is then obtained by reaction of the DMK derivative with the appropriate anhydrous acid, HCl, HBr or HI.

The peptide intermediate starting materials can in turn be synthesized, either by solid phase synthesis or classical methods, or a combination of the techniques. In general, for peptides longer than a three-amino acid sequence, solid phase techniques can be employed; however, some synthesis of intermediates by classical methods will usually be required.

In the preparation of the TRF intermediate described above, pyroglutamyl histidine methyl ester is obtainable by either the direct reaction of pyroglutamic acid with histidine methyl ester in DCCI, or preferably, for improved yields, by the reaction of carbobenzoxy-pyroglutamic acid in the form of a mixed anhydride. In the former method, yields are improved if tetrahydrofuran (THF) is employed as solvent with just sufficient DMF to dissolve the pyroglutamic acid reactant.

Since the synthesis of LRH cannot be conveniently achieved by solid state techniques alone, the total synthesis employs a combination of solid state and classical techniques, such as described by H. Sievertson, H. et al. in Journal of Med. Chem (1972) 15 222. Briefly, the initial three amino acids are coupled together by classical techniques to produce the tripeptide pGlu.His.Trp, and the remaining seven amino acids coupled by solid phase method to produce the protected heptapeptide Ser(Bzl).Tyr(Bzl).Gly.Leu.Arg(NO$_2$).Pro.Gly.OMe. In theory, the two peptides can then be coupled by activation of the acyl group of the tripeptide with DCCI and 1-hydroxybenzotriazole followed by condensation of the activated tripeptide with the heptapeptide to form the methyl ester. The peptide ester is then de-protected by removal of the benzyl and nitro groups by catalytic hydrogenolysis, followed by saponification to form the LRH free acid.

In preparing the peptide intermediates and peptide precursors of the invention, care must be exercised to minimize racemization of the amino acid residues. Various methods are known for protecting the materials from racemization; for example, tert-butoxycarbonyl (BOC) or carbobenzoxyfuran are useful as protecting groups, particularly for proline or pyroglutamic acid. A discussion of blocking groups useful in the systematic assembly of a peptide sequence, and methods useful for cleaving these groups after assembly of the sequence is found for example in U.S. Pat. No. 3,853,834 to Shields, issued Dec. 10, 1974. Other teachings relating to the synthesis of pyroglutamyl peptides are found in U.S. Pat. No. 3,752,800 to Wissmann et al (Aug. 14, 1973); U.S. Pat. No. 3,753,969 to Folkers et al (Aug. 21, 1973); U.S. Pat. No. 3,966,700 to Mattalia (June 29, 1976); U.S. Pat. No. 3,988,307 to Gross (Oct. 26, 1976); U.S. Pat. No. 4,060,603 to Morgan et al (Nov. 29, 1977); U.S. Pat. No. 3,824,227 to Ries et al (July 16, 1974); U.S. Pat. No. 3,813,382 to McKinley et al (May 28, 1974); U.S. Pat. No. 3,931,139 to Wissmann et al (Jan. 6, 1976); and U.S. Pat. No. 3,959,248 to Veber et al (May 25, 1976). The principles of this prior art are applicable to the assembly of peptide sequences other than pyroglutamyl-terminal peptides, as well.

The agonist and antagonist activity of the derivatives of the invention on the activity of the corresponding precursor polypeptides in mammals is measurable by various known bioassays. In instances where the free acid form of the peptide precursor is biologically inactive, such as in TRF and LRH, the free acid is conveniently employed as a negative control in these tests. Useful bioassay procedures include the classic McKenzee bioassay for release of radioactive $^{125}I$ as a test of the potency of TRH derivatives of the invention.

The derivatives of the invention accordingly are broadly applicable in regulation or alteration of pituitary function by interference with the normal activity of the hypothalamic factors or the opiate peptides. In addition to therapeutic applications, the derivatives are useful as investigative tools, for example as covalent probes wherein the HMK and DMK derivatives of the invention are radioactively labelled to provide affinity for the receptor site. Topographical mapping of membrane receptors under varying physiologic conditions is thus possible by use of autoradiography in conjunction with the use of radioactively labelled derivatives, such as $^{14}C$-diazomethane derivatives of TRH. Further, the derivatives are useful as covalent probes in the evaluation of the relationship between hypothalamic peptides and opiate peptides (neuropeptides) and their respective roles in the regulation of pituitary hormones and in the central nervous system. Additional uses include the use of the derivatives, especially the antagonists, in identifying the role the precursor peptide plays in the synthesis and/or release of certain pituitary hormones by negating the activity of the precursor peptide.

BEST MODE PROCEDURES

In order to minimize racemization and provide a good product yield, the α-amino acid sequence of the precursor peptide is conveniently obtained according to the Merrifield Solid Phase Technique, described fully in *J. Am. Chem. Soc.* 85 2194 (1963). When the free acid of the peptide is desired, chloromethylated or hydroxymethylated resins are typically employed; when the amide of the peptide is desired, a benzhydryl-amine resin is useful.

In the solid phase method, an N-protected amino acid is bound to a resin by esterification (Eq. 1). The protective group is removed and a second N-protected amino acid is coupled to the amino group of the resin-bound amino acid (Eq. 2). All side products and unreacted soluble materials are washed out of the resin, the N-protecting group is cleaved, and the coupling step is repeated with a third N-protected amino acid (Eq. 3). The process is continued until the synthesis is complete. The peptide is now cleaved from the resin (Eq. 4) and purified by conventional techniques (Gel Filtration/Partition Gel Filtration)

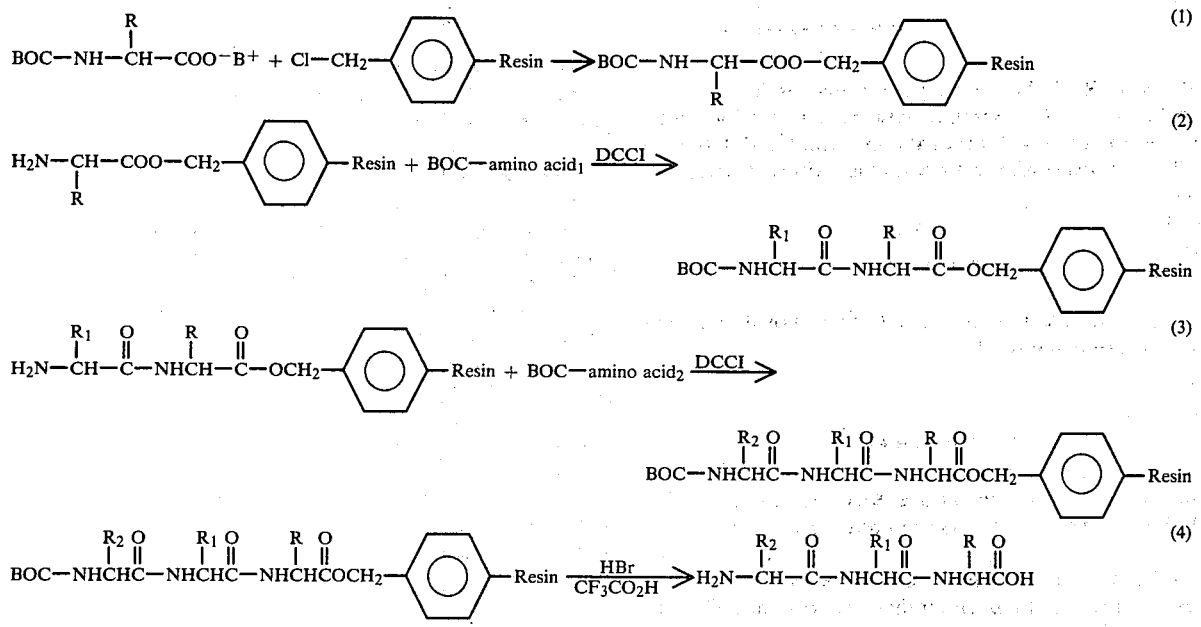

The resin employed is a copolymer of 98% styrene and 2% divinylbenzene. To provide a reactive group for attachment of the first amino acid, the benzene rings of the resin are partially chloromethylated (Bio Beads S-X-2, 200-400 Mesh, capacity 0.72 mEq/gm), and when this chloromethylated resin is treated with triethylamine salt or cesium salt of an N-protected amino acid, a benzyl ester-type bond is formed. Such a bond is stable during the synthetic steps, but can be cleaved with HBr in acetic acid or trifluoroacetic acid, which simultaneously removes the N-protecting group and cleaves the peptide from the resin (Eq. 4).

The coupling reagent most widely used is dicyclohexyl carbodimide (DCCI). In methylene chloride as the solvent, and about a 250% excess of the t-BOC amino acid and DCCI, the reaction is complete. Dimethylformamide is also used as solvent. Active esters of the α-amino acids, such as N-OH-succinamide, p-nitrophenyl and pentachlorophenyl esters, are useful in the synthesis to decrease racemization of the product; 1-hydroxybenzotriazole has been used in conjunction with these esters as catalyst for the condensation. The diazomethylketones and halomethylketones are then prepared from the free acid peptide product as previously described.

The procedure most frequently used for TRH, TRH free acid, or TRH structured analogues is outlined as follows:

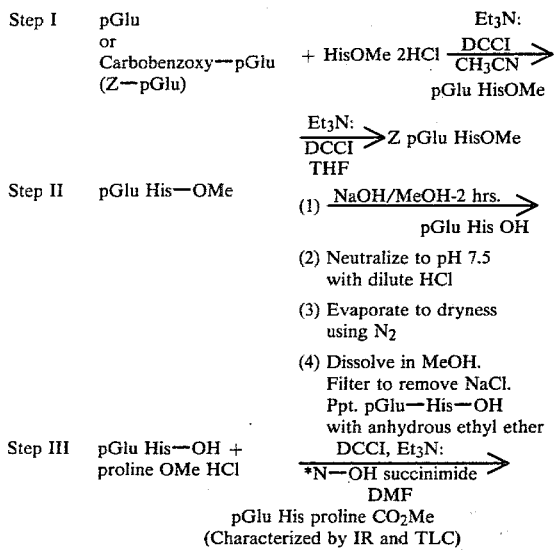

*N—OH succinimide was used to make active ester of pGlu His OH in order to prevent epimerization about the α-carbon of histidine, which in the peptide sequence is most vulnerable to racemization To minimize racemization, the triethylamine is omitted, and N,N-diisopropylethylamine or N-ethyl morpholine is used, or, alternatively, the dicyclohexylamine salt of pGlu His OH is employed (pGlu His DCHA). The DCHA will combine with HCl derived from proline OMe HCl to form the insoluble organic salt DCHA HCl.

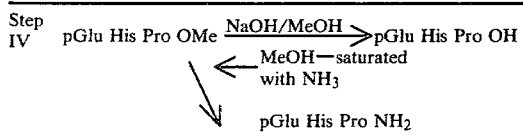

The pGlu-His-Pro OMe of good quality is used to make TRH-DMK or TRH-HMK as follows:

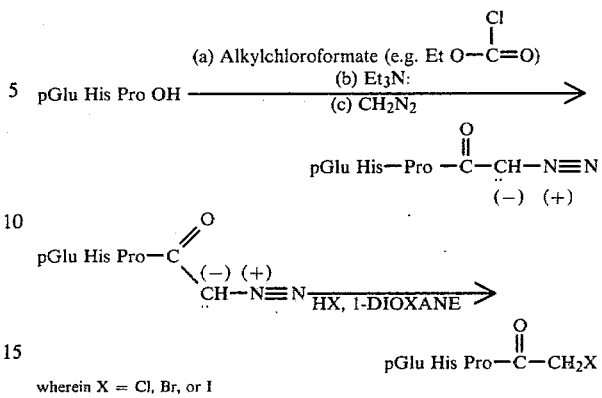

wherein X = Cl, Br, or I

TRH-HMK is alternatively synthesized by the following method.

The dipeptide methyl ester is saponified to the dipeptide free acid, treated with dicyclohexylamine to form the dicyclohexylamine salt, and then coupled directly to proline halomethylketone using DCCI with dimethylformamide as solvent. The proline halomethylketone is prepared by converting tert-BOC proline to a mixed anhydride using ethylchloroformate and triethylamine in anhydrous ethyl ether, and then reacting with diazomethane. The diazomethane product is reacted with HX, for example, with anhydrous HCl at $-10°$ C. for 2 hours with ether as the solvent. The oily residue, which results after evaporation with nitrogen, is dissolved in methanolic HCl, and taken to a thick syrup under reduced pressure. A solid compound formed upon addition of absolute ethanol. The solid formed a crystalline compound when it was dissolved in 95% ethanol and overlayed carefully with anhydrous diethyl ether. The

derivative gives a strong absorption peak at 1742 cm$^{-1}$ (C=O carbonyl stretch) in the IR, which is characteristic of halomethylketones (P. L. Birch et al, *Archives of Biochem. and Biophysics* 148: 447–451 (1972)). The chloromethylketone derivative was prepared from

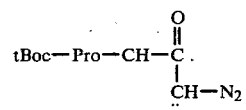

The NMR spectrum showed a peak positioned at α=4.25 ppm (2H,

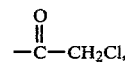

CDCl$_3$, Me$_4$Si). The NMR spectrum for

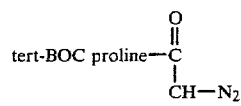

showed peaks positioned at α=1.40 ppm (tert-BOC), α=1.86 ppm (a-H), α=3.36 ppm (b-H), α=4.13 (CH) and α=5.41 ppm

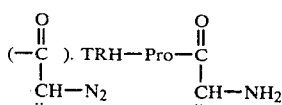

was prepared from the

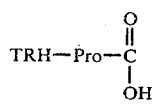

(free acid) by reacting the free acid with an alkylchloroformate with Et₃N: as the base, and anhydrous ether as the solvent to form an activated carboxylic acid derivative (e.g., anhydride). This activated derivative was then reacted with ethereal diazomethane that was prepared from N-methyl-N-nitroso-p-toluenesulfonamide. When the solvent was removed with nitrogen, a yellow solid resulted that showed absorption frequencies at 2100 cm$^{-1}$ (diazo) and 1634 cm$^{-1}$ (carbonyl) in the IR.

I. A. PGlu-His-OMe. (J. Boler, K. Folkers, J. Med. Chem. 14, 475 (1971)).

His-OMe-2HCl (1.2 g) and pGlu (0.64 g) in dry MeCN (20 ml) were treated with 1.4 ml of Et₃N and 1.24 g of DCCI in dry MeCN (3 ml) at 0° C. After being stirred at room temperature for 24 hrs., the reaction mixture was filtered. The white precipitate collected was washed with fresh MeCN, dissolved in purified methanol and the Et₃ N HCl and dicyclohexylurea removed by filtration. The mother liquor was then put in a freezer at −20° C. to remove additional dicyclohexylurea and anhydrous ethyl ether was added to precipitate pGlu His OMe. The product was re-crystallized from methanol to yield 0.65 to 0.90 grams of pure pGlu His OMe (55% yield) m.p. 210° C.–212° IR: 1750 cm$^{-1}$ (ester C=O), 1680 cm$^{-1}$ (lactam C=O) and 1670 cm$^{-1}$ (amide C=O). NMR: S=3.44 ppm(s, 3, OCH₃) when D₂O was used as the solvent TLC: R$_f$=0.72 CHCl₃:CH₃OH: 38% AcOH (60:45:20). R$_f$=0.53 Butanol:AcOH:H₂O:Pyridine (60:12:48:40). Silica gel G, Pauley positive (diazosulfanilic acid reaction) spots. Mass spec. (electron impact): M/e=280 (molecular ion)

B. Preparation of pGlu His OH 280 mg of pyroGlu His OMe was dissolved in 3 ml of MeOH to which was added 1.3 ml of 1 N NaOH. The saponification was followed by TLC, and after 90 minutes, complete reaction had taken place, and the mixture was neutralized by addition of 1.3 ml of 1 N HCl and evaporated to complete dryness in vacuo. The solid residue was thoroughly suspended in 5 ml of purified DMF and filtered through a cotton plug into round bottom flask. The dipeptide was then coupled directly to proline OMe HCl.

Dansylated TRH Pro CO₂H (TRH free acid) Hydrolysate

Developing solvent (1.5/100 v/v) 90% Formic Acid/H₂O

Support—Polyamide plates (5×5 cm).

| | R$_f$ |
|---|---|
| Dansyl amino acid | |
| his | .13 |
| pro | .45 |
| glu | .50 |
| TRH Pro CO₂H | |
| HYdrolysate | .125 |
| | .44 |
| | .50 |

TRH Diazomethylketone was prepared from the free acid by reacting the free acid with an alkylchloroformate, such as

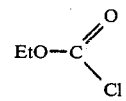

using either diisopropylethylamine or triethylamine as a base and ether/THF as the solvent. The activated carboxyl of the tripeptide, pyroGluHisPro-CO₂H, was then reacted with ethereal diazomethane prepared from N-methyl-N-nitrogen-p-toluene sulfonamide to give a yellow oil (solid at −20° C.) having the following characteristic diazo- and carbonyl frequencies in the IR: 2100 cm$^{-1}$ and 1634 cm$^{-1}$.

Procedure:

The free acid, TRH CO₂H, saponified by the procedure indicated above was purified using Dowex 50 (H) ion exchange using the batch technique prior to running the diazomethane reaction. 5 mmoles of the tripeptide free acid was reacted with 5 mmoles of triethylamine, cooled to −15° C. in THF and then 15 mmoles of ethylchloroformate was added. The reaction was then allowed to run for 20 minutes. The reaction mixture was filtered and the filtrate added to freshly prepared diazomethane. Reaction was then allowed to run overnight at −10° C., after which evaporation to reduce volume with nitrogen left a yellow compound, which was a solid at −20° C. The TRH Pro CH₂Cl (TRH proline chloromethylketone) was formed by addition of 4 M HCl dioxane. A white compound resulted upon precipitation with ether.

C. Preparation of pGlu His Pro CO₂Me 7.6 mmoles (2 g) of pyroglutamylhistidine free acid and 7.6 mmoles of N—OH succinimide (0.874 g) were dissolved in DMF. The solution was cooled to 0° C. and 1.568 g (7.6 mmoles) of DCCI in 1-2 ml of DMF were added. 1.25 g of proline.OMe.HCl was added and the reaction was stirred overnight between 0° and 10° C. The reaction mixture was filtered to remove the dicyclohexylurea and then evaporated under nitrogen. (R$_f$=0.53 Silica Gel G Solvent 66% MeOH in CHCl₃). The tripeptide methyl ester was purified using Bio-Gel P-2 (200-400) Gel Exclusion chromatography (39 cm×2.4 cm column).

The elution solvent was a 0.25 N AcOH and Pauly Positive fractions were pooled and lyophilized. Saponification to obtain the free acid was carried out in the usual manner. (See "B").

D. Characterization of TRH CO₂H

| | | Conc. (n moles/ml) | Molar Ratio |
|---|---|---|---|
| Ion Exchange Chromatography: | Histidine | 247.86 | 1.37 |
| | Glutamic | 181.08 | 1.00 |
| | Proline | 203.84 | 1.13 |

-continued

| (Mass Spect. Studies of TRH Free Acid (Electron Impact)) | | |
|---|---|---|
| | | m/e |
| 1. | Pyrrolidine Ring (Prolyl less one C=O) | 70 |
| 2. | Prolyl with carbonyl | 97 |
| 3. | Pyroglu | 112 |
| 4. | Pyrrolidone Ring | 84 |
| 5. | Imidazole + $CH_2$ | 81, 82 |
| 6. | Histidine | 137 |
| 7. | Histidyl Ring | 67 |
| 8. | Diketopiperazine of his + pro | 234 |

II. Synthesis of cyclopentoylhistidine proline free acid

To the free base of Histidine methyl ester dihydrochloride, (m.p. 206°-207° C.), 2 mmoles of cyclopentane carboxylic acid and 2.2 mmoles of DCCI were added. The resulting dipeptide was purified by preparatory TLC with $CHCl_3$/MeOH (7/1) as the stationary phase. An oily residue was obtained, which was then dissolved in dioxane and hydrolyzed by NaOH. After acidification to neutralize and lyophilization, the residue was treated with dry purified methanol and filtered to remove insoluble sodium chloride. The product was coupled in dimethylformamide with proline using DCCI and 1-hydroxy-benzotriazole. The reaction mixture after 48 hours in an ice-salt bath (−10° C.) was immediately applied to a Sephadex G-≈column, and purified by gel filtration column chromatography. Fractions eluted from the column that showed a positive Pauley reaction (diazo sulfanillic acid reaction) were pooled together and lyophilized. A white fluffy product results. Yield-(30-40%).

III. A. Bioassay of TRH-Diazomethylketone

Long-Evans male rats weighing approx. 200 gm. each were kept on an iodine free diet for two weeks. Twenty-four hours before the bioassay was performed, the animals were injected intraperitoneally with 25 μCi of $Na^{125}I$. Six hours before the bioassay was performed, the animals were given 0.03% propylthiouracil in their drinking water. The animals at assay time were challenged with various concentrations of TRH (positive control) and TRH-$CO_2H$ (negative control) by injecting into the tail vein. At two hours, blood samples were taken from the tail vein and 40 μgm of TRH.Diazomethylketone was injected into the tail vein. One hour later, blood samples were again taken. All samples were counted for their $^{125}I$ content using a γ-spectrometer.

In FIG. 1, Curve No. 1 represents the dose-response curve when TRH was given. Curve No. 2 shows a dramatic inhibition in releasing activity by TRH after injection of TRH-Diazomethylketone. Curve No. 3 (when compared to Curve 2) illustrates that some relief of inhibition occurs when the animals are given TSH. Curve No. 4 represents the dose-response curve of a biologically-inactive derivative of TRH, the free acid form.

Conclusion: The inhibition of releasing activity caused by TRH-DMK is not significantly affected by giving TRH following tail vein injection of TRH-DMK. TRH-DMK apparently acts at the level of the pituitary to inhibit the release of TSH from this anatomical site. TSH will partially relieve the inhibition by TRH-DMK. This study illustrates the specificity of action of TRH-DMK at the pituitary level.

B. Bioassay of TRH-Chloromethylketone

The procedure in Example III A. was followed with TRH-Chloromethylketone used in place of TRH-diazomethylketone.

Figure 2:
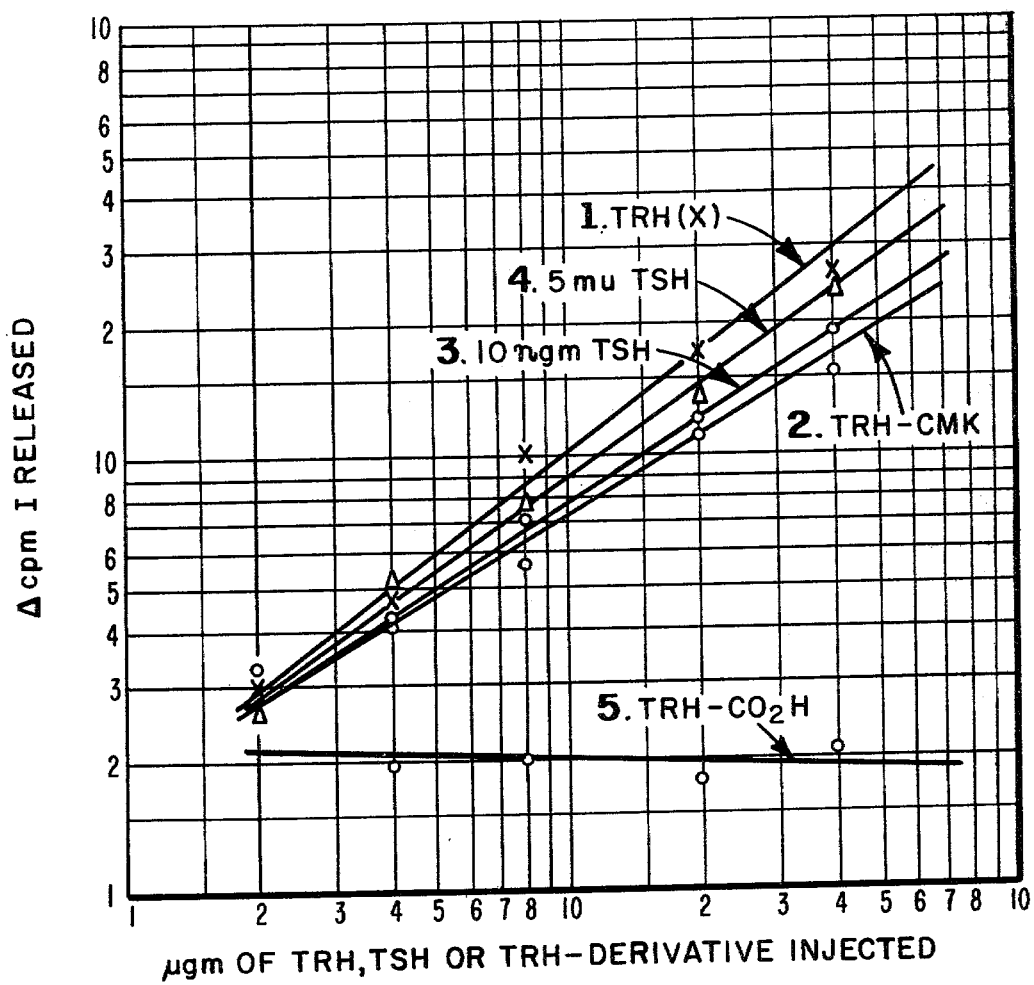
FIG. 2 is a graphic evaluation of a TRH-HMK bioassay.

As seen in FIG. 2, TRH-chloromethylketone causes some inhibition of TRH releasing activity, since the slope of curve 2 is less than that of curve 1. When either 5 mU of TSH or 10 μgm TRH are given following administration of TRH-CMK via the tail vein, some increase in slope does occur, but the slope is never the same as the slope of curve 1. Curve No. 5 represents the negative control (no TRH releasing activity).

IV. Radioimmunoassay Procedure for Determination of Serum Thyrotropin and Prolactin Prolactin secretion is controlled in part by factors of hypothalamic origin; its secretion is stimulated by TSH and suppressed by Prolactin Inhibitory Factors (PIF). The increase in serum prolactin is often associated with hypothalamic and pituitary tumors, galactorrhea, or amenorrhea with and without galactorrhea. The basal prolactin levels in the Long-Evans rat as established by RIA is 20-40 ng/ml. $^{125}I$-labeled rat prolactin or TSH, prepared by the labeling of highly purified rat prolactin (NIAMDD*-Rat TSH or PRL-I-3), is designed for use in the radioimmunoassay of prolactin or thyrotropin stimulating hormone in biological fluids (e.g. serum derived from blood collected via tail vein of the rat). The radioactive hormone is used in in vitro incubations with a specific antiserum (NIAMDD-Anti-Rat Prolactin or TSH serum) and the hormone standard (NIAMDD-Rat PRL-RP-1 or NIAMDD-Rat TSH-RP-1), or unknown samples. In this system, the radioactive and non-radioactive hormone compete for a limited number of antigen binding sites on the antibody molecule in the manner represented below:

$$\frac{AB}{^{125}I\text{-PRL (or }^{125}I\text{-TSH)} + \text{Anti-PRL antibody}}$$
Non-radioactive PRL     (Anti-TSH antibody)
(or TSH)

$^{125}I$-Prolactin-AB + PRL-AB Complex
or (Rs I-TSH-AB            or
complex)              (TSH-AB Complex)

* National Institute of Arthritis, Metabolism, & Digestive Diseases

Figure 10:
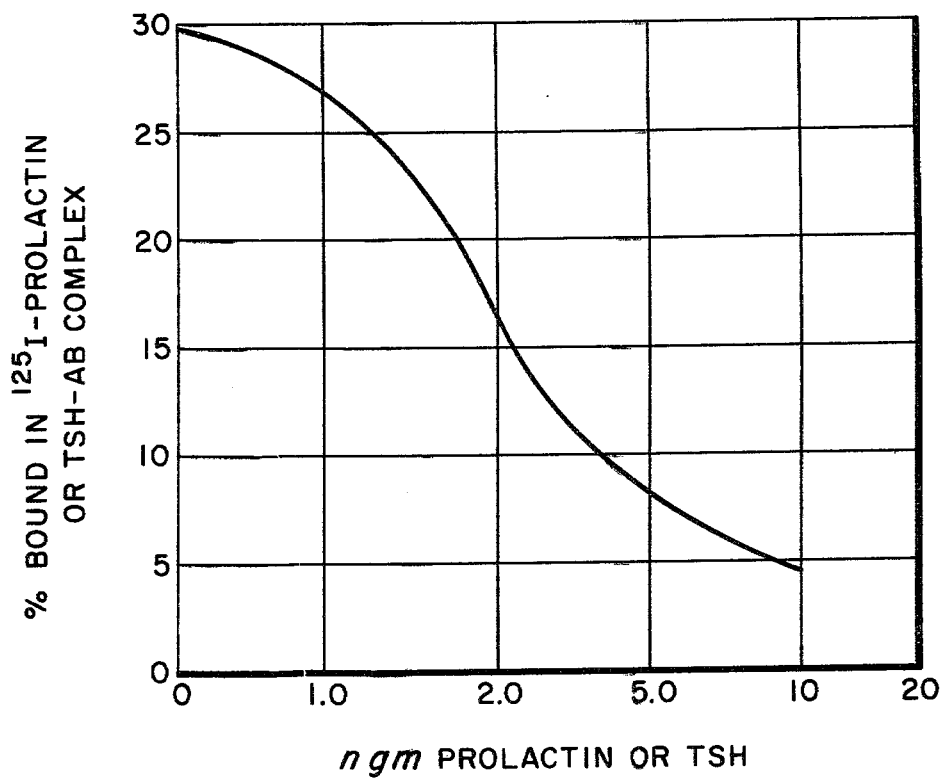
FIG. 10 is a graphic illustration of a standard curve.

The quantity of $^{125}I$-PRL-AB complex (or $^{125}I$-TSH complex) formed in the reaction gives rise to an inverse relationship to the amount of non-radioactive hormone present. Thus, a standard curve may be constructed from which the quantity of prolactin or TSH in an unknown sample may be determined as illustrated in FIG. 10.

In practice, the hormone antibody complex is separated by the addition of a second antibody which binds to and precipitates quantitatively the radioactive hormone-AB complex from solution. The latter is separated by centrifugation and the precipitated radioactivity counted in a gamma (γ) scintillation counter.

| | 6 Point Dose-Response Curve on Inter-Triplicate Assays | | |
|---|---|---|---|
| TRH | TSH-RP-1 ng/ml (1 hr.) post inject | PRL-RB-1 ng/ml (1 hr.) post inject | |
| saline (tail vein) | 387,393,379 | 49,61,53 | Cardiac Aspiration |
| 0.4 mg | 412,408,422 | 71,64,68 | 200g Long-Evans Rat |
| 4 | 500,516,531 | 96,112,84 | |
| 40 | 875,729,785 | 216,234,208 | |
| 80 | 1901,1997,1976 | 396,381,406 | |

-continued

| 6 Point Dose-Response Curve on Inter-Triplicate Assays | | |
| --- | --- | --- |
| TRH | TSH-RP-1 ng/ml (1 hr.) post inject | PRL-RB-1 ng/ml (1 hr.) post inject |
| 200 | 2005,2130,2168 | 412,399,420 |

*200 μg TRH-Diazomethylketone injected tail vein after collecting saline control sample, blood-samples collected by cardiac aspiration at 1 hr.

| saline | 379,256,279 | 55,71,49 |
| --- | --- | --- |
| 0.4 | 516,279,456 | 73,76,69 |
| 4 | 568,412,509 | 86,107,82 |
| 40 | 612,661,599 | 199,219,169 |
| 80 | 718,699,756 | 231,275,255 |
| 200 | 730,899,798 | 296,285,283 |

*200 μg TRH-Chloromethylketone injected into tail vein after collecting saline control sample, blood samples by cardiac puncture.

| saline | 279,246,301 | 35,38,42 |
| --- | --- | --- |
| 0.4 | 316,299,350 | 69,65,56 |
| 4 | 426,396,416 | 82,79,81 |
| 40 | 699,599,567 | 198,201,175 |
| 80 | 1315,1261,1038 | 361,342,359 |
| 200 | 1611,1489,1541 | 403,359,398 |

Summary of data given in the 6 Point Dose-Response Curve on Intertriplicate Assays.

The three figures represent the results of analysis by radioimmunological assay of blood samples from 3 different animals which were subjected to the treatment described in the first column. The three values for the TSH levels correspond to the 3 values for prolactin which was measured on the same sample of blood from each animal.

V. Assay Procedure For Determination of Enkephalin Activity

The guinea pig ileum, especially the myenteric plexus-longitudinal muscle preparation has been widely used as an in vitro model for the study of the mode of action of morphine-like drugs. This is primarily due to the similarity of the opiate receptors in the myenteric plexus to those found in the Central Nervous System.

It has been found that the sensitivity of this method to opiates is similar to that found in the Central Nervous System in the following aspects: (1) the effective concentrations of morphine are low; (2) the rank order of potencies of various narcotic agonists and antagonists are similar; (3) the response to narcotic agonists is stereospecific; (4) narcotic antagonists block the effect of narcotic agonists, which is also stereospecific; and (5) the myenteric plexus develops tolerance and dependence. METHOD: Electrical stimulation of the guinea pig ileum evokes release of acetylcholine (ACh) from the myenteric plexus, which in turn elicits a contracture of the muscle. Narcotic analgesics block the evoked release of acetyl choline from cholinergic motorneurons, and morphine antagonists like naloxone can reverse this effect.

Figure 3:
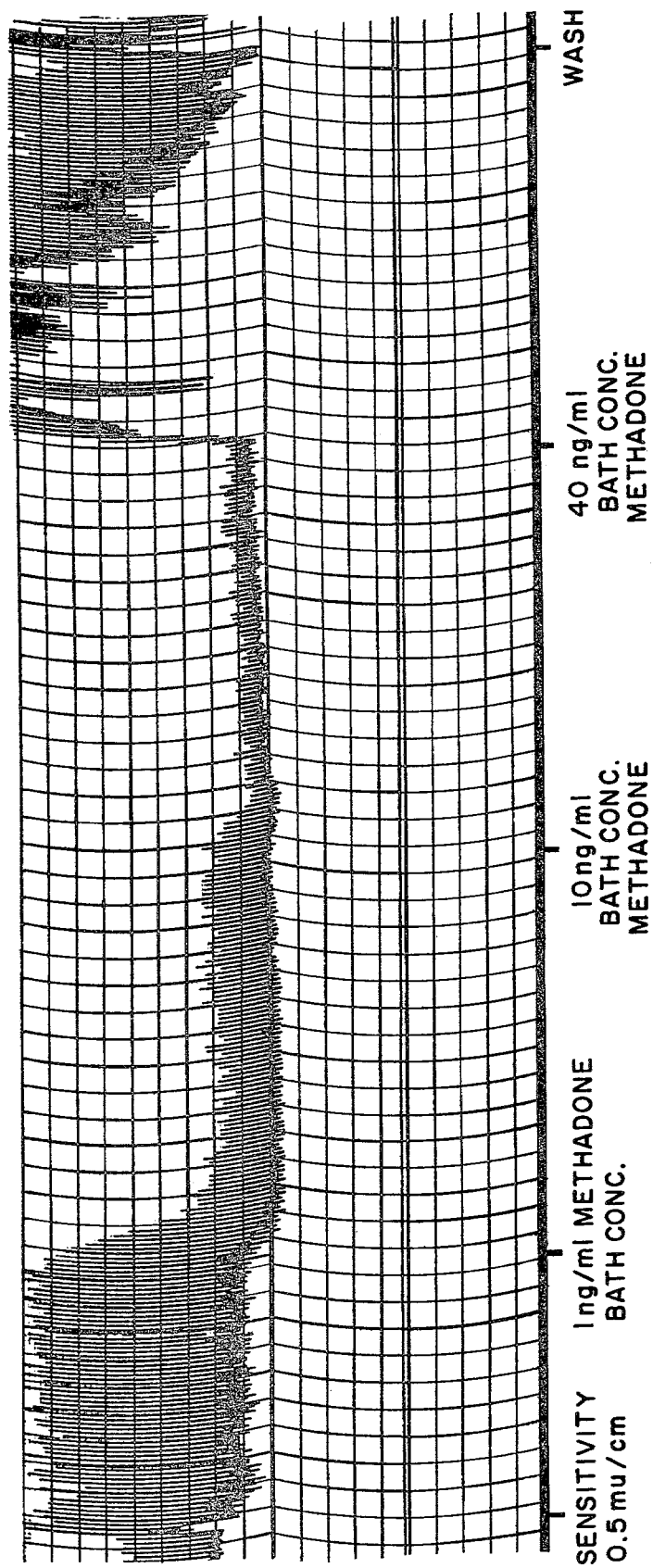
FIGS. 3-9 are Grass polygraph displays of muscle activity in enkephalin bioassays.

The ileum (from guinea pigs weighing between 200–300 g) was cut about 10 cm from the caecum and cut again about 30-40 cm from that point. The contents of the intestine was expelled by flushing with Tyrode's solution and a piece 2–3 cm in length cut from the end closest to the caecum. This piece of tissue was then impaled on the two prongs of the electrode (which was connected to the stimulator) and one end tied with a piece of thread which was then attached to a force transducer. The assembly was placed in a 100 ml organ bath at 37 degrees C. containing Tyrode's solution gassed with 95% $O_2$, 5% $CO_2$. Electrical stimulation (rate: 0.2 Hz, duration: 0.4 msec, voltage: 60 volts) then evoked the release of ACh which in turn causes the muscle to contract. The force transducer then converts these muscle contractions to electrical pulses which the Grass polygraph displays. RESULTS: FIG. 3 shows the typical assay results for Methadone—a synthetic opiate used to standardize the GPI assay. Initially the electrical stimulation produce contractions in a rhythmic fashion to give rise to the trace at the left. When Methadone is added to the tissue bath such that the concentration of Methadone in the bath is 1 nanogram/ml an immediate decrease in the height of the contractions is noted. As the concentration of Methadone is increased, the contraction height is decreased. Finally, when Naloxone (an opiate antagonist) is added to the bath the contractions immediately return indicating that Naloxone has displaced Methadone at the opiate receptor site thus allowing the electrical stimulation to again release ACh and cause contractions.

Figure 4:
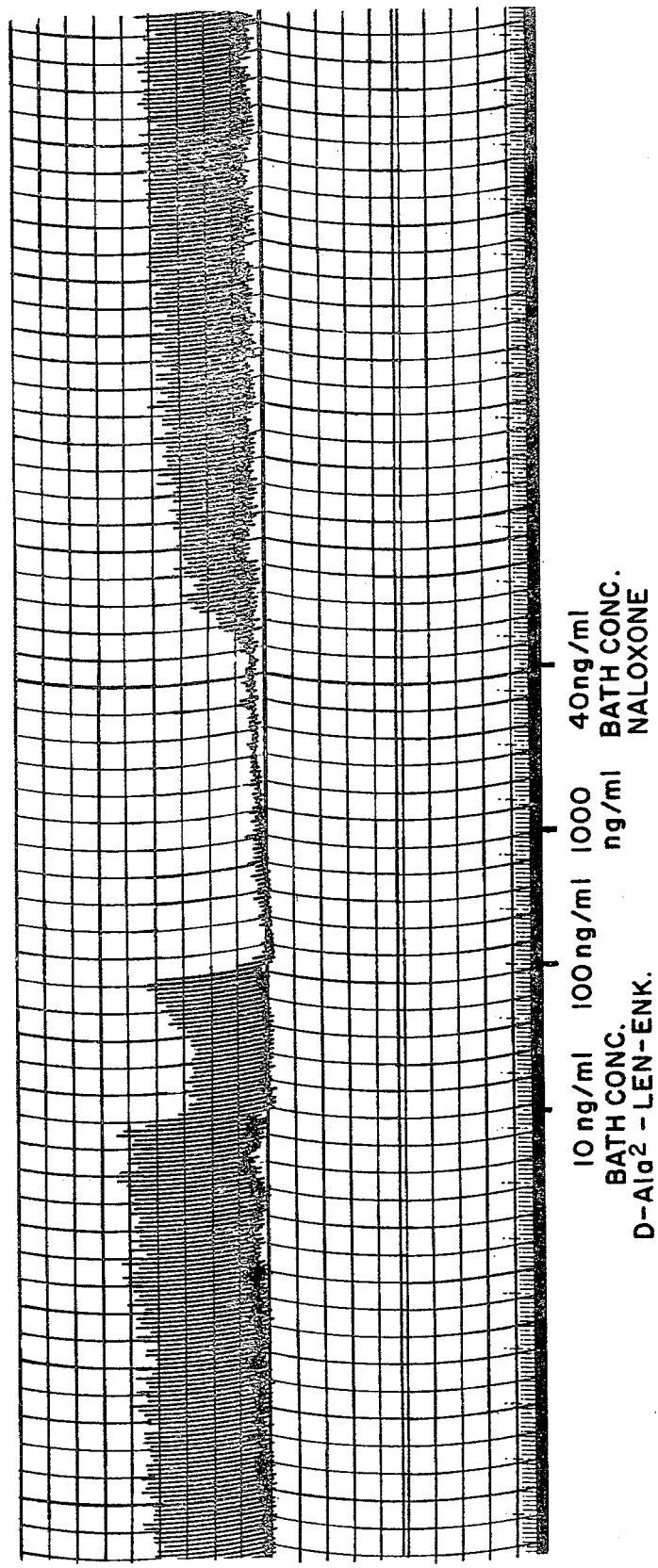

FIG. 4 shows a typical response to an enkephalin-[D-Ala$^{(2)}$-Leucine Enkephalin]. At 10 ng/ml one obtains about a 50% reduction in the height of the GPL contractions. At 100 ng/ml the reduction in the height of contractions is essentially complete and only "background" noise is observed. When Naloxone is again added—even in the presence of a total of 1,110 ng enkephalin—the contractions immediately return. Thus the enkephalins appear to act in a manner similar to the opiates and in a Naloxone-reversible fashion.

Figure 5:
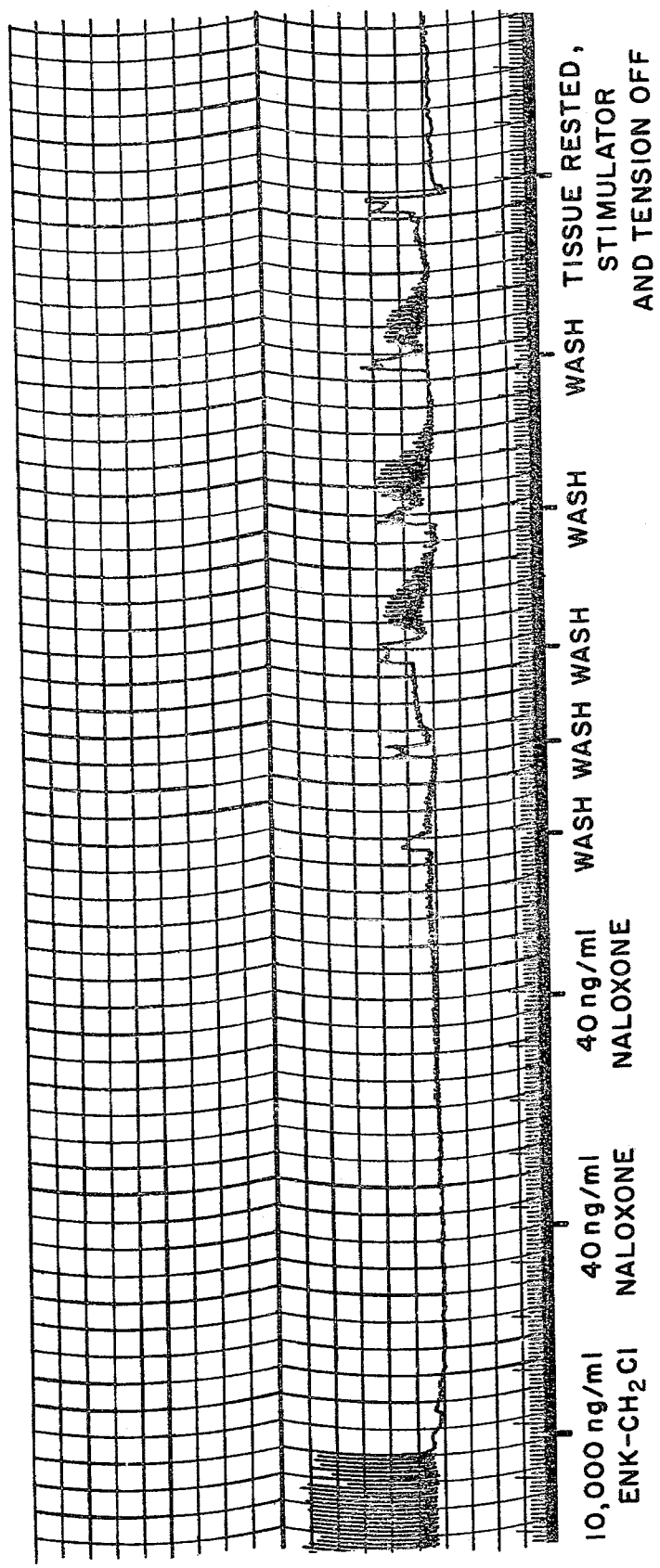
Figure 6:
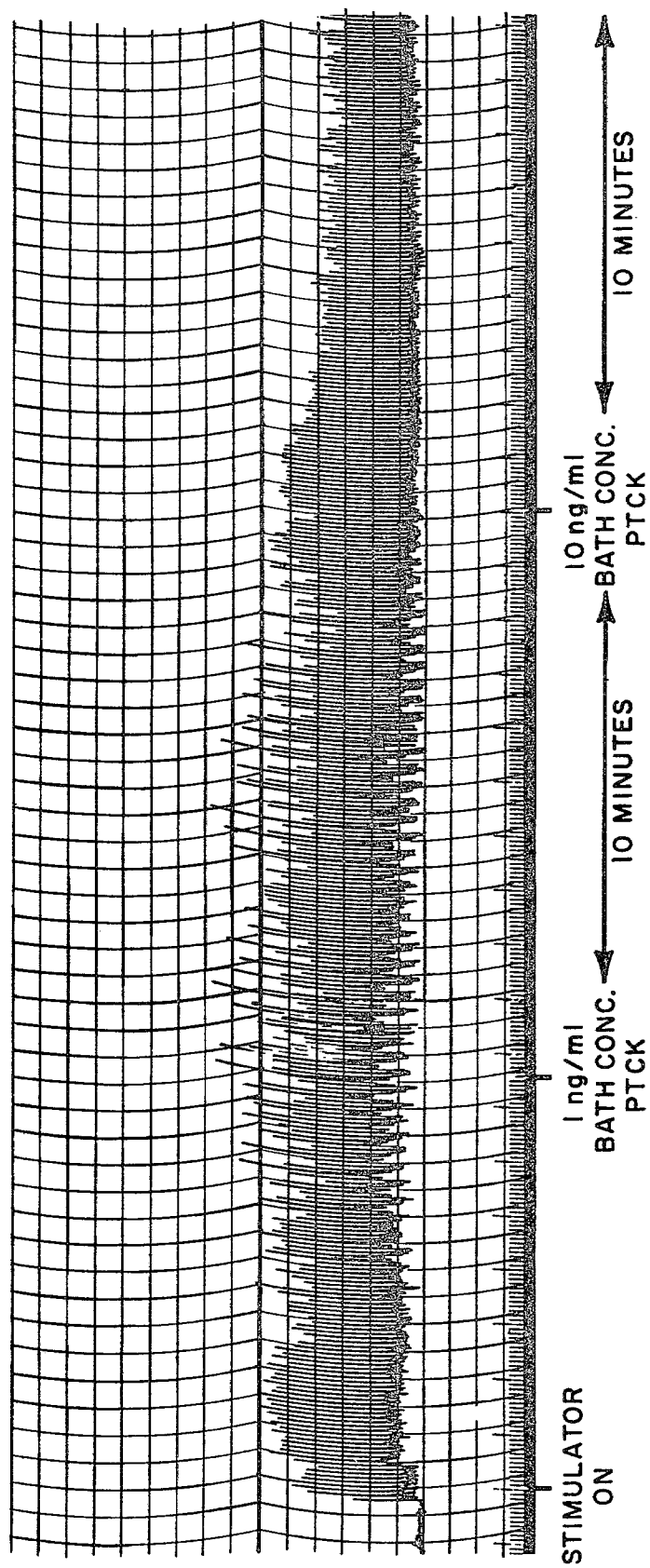
Figure 7:
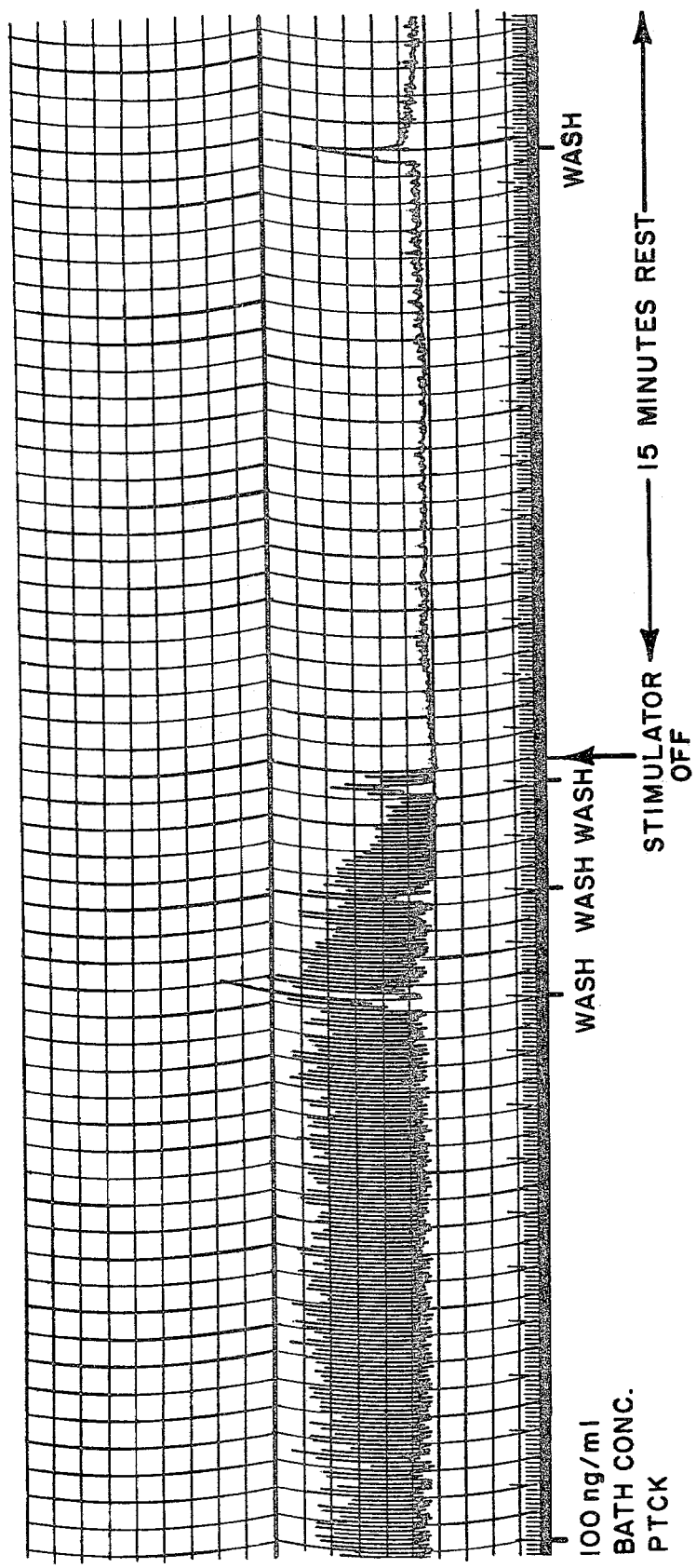
Figure 8:
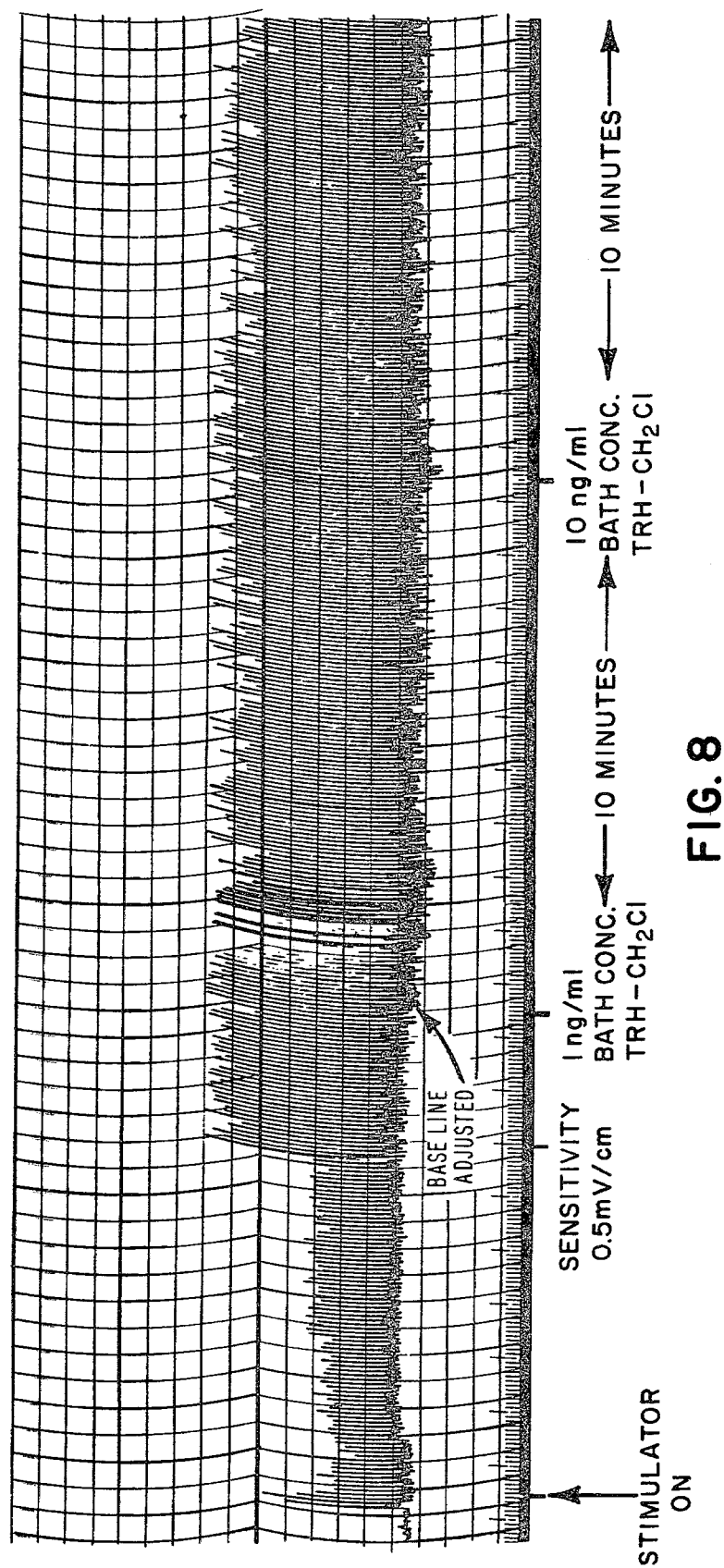
Figure 9:
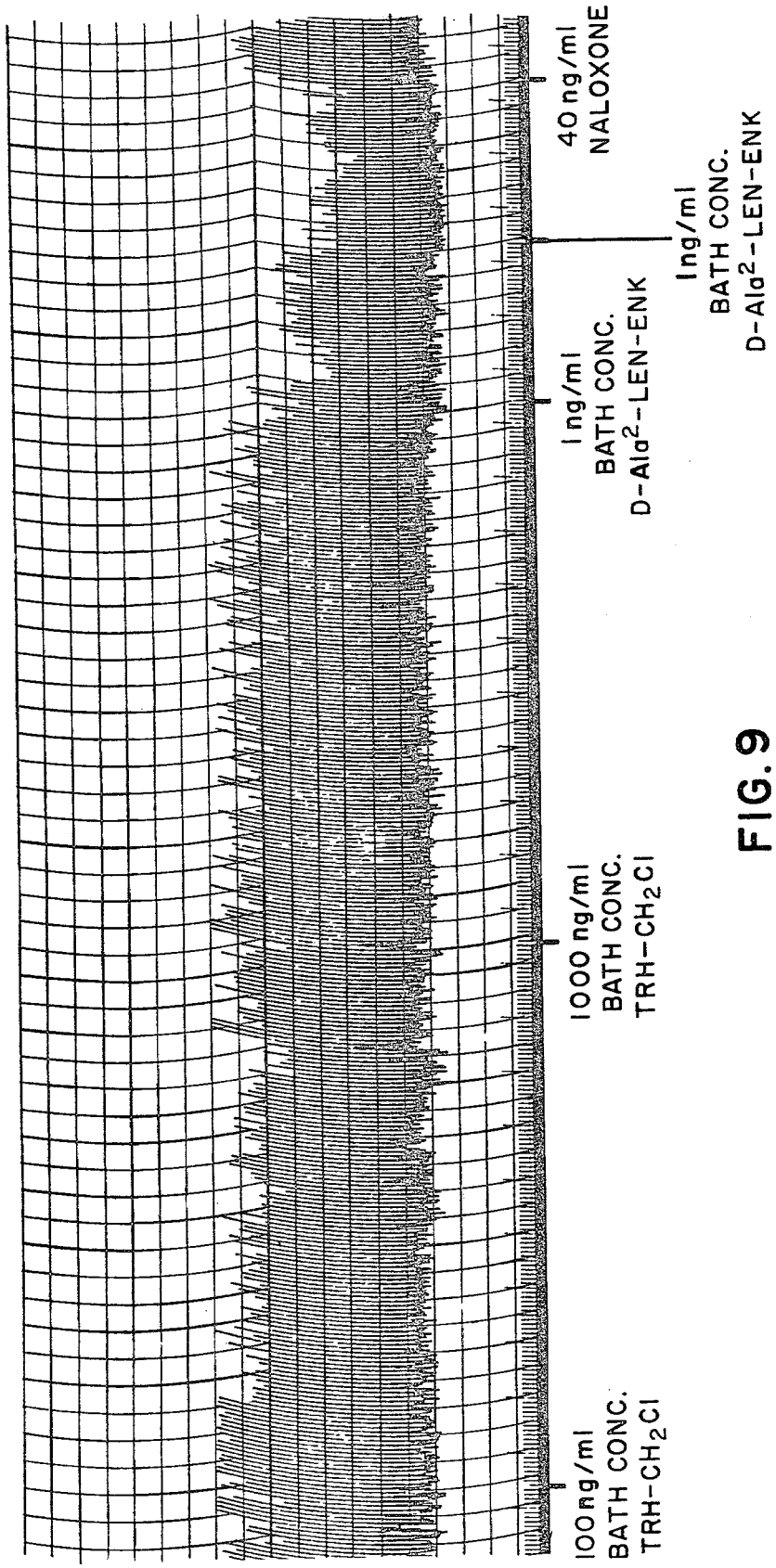

FIG. 5 shows the results of adding an enkephalin chloromethylketone to the tissue bath. In this experiment, 10,000 ng/ml of D-Ala$^{(2)}$-Leucine enkephalin chloromethylketone completely blocked the electrically stimulated release of acetylcholine from the Guinea Pig Ileum (GPI). Further, after several additions of Naloxone and repeated washings this blocking effect is still apparent. From this it would appear that the enkephalin chloromethylketone does indeed bind irreversibly to the receptor site.

FIGS. 6–9 show the effects of two other chloromethylketones on the GPI. Since neither the N-tosylphenylalanine chloromethyl ketone (PTCK, an amino acid chloromethylketone) nor Thyroid Releasing Hormone chloromethyl ketone appear to effect a response, the effect of the enkephalin derivative would appear to be a specific one. Thus what is seen in FIG. 5 is not the result of, for example, non-specific alkylation by the chloromethyl ketone but rather a specific interaction with the opiate receptor site.

VI. McKenzie Bioassay for TRH-Induced Release of Radioactive ($^{125}$I) Iodide from the Thyroid 16 Long-Evans male rats were maintained on an iodine deficient diet for 1 week. Each rat was then injected intraperitoneally (i.p.) with 20 μCi of radioactive (Na$^{125}$I). Six hours before injection of the material to be tested, the animals were given 0.03% propylthiouracil (PTU) in their drinking water. This prevents the reuptake of released $^{125}$I (iodoproteins such as mono- and diiodo-tyrosines, T$_3$ or T$_4$) once they are released from the thyroid under the influence of TRH or TRH analogue. 24 hrs. after administration of the radioactive iodine (0.2 ml) 200 μl of blood was withdrawn from the tail vein of each rat, transferred quantitatively into a 12×75 mm test tube containing 1 ml of 0.9% saline and the $^{125}$I content counted by use of a Beckmann γ-ray spectrometer. One ml of TRH or TRH analogue dissolved in 0.9% NaCl (physiologic saline) was injected into the tail vein of each of four rats per dose considered (e.g. 0.4 μgm, 40 μgm, 80 μgm). 1 ml of 0.9% NaCl (physiologic saline) was injected also to each of four rats to serve as a control for stress-related influence (trauma from blood collecting procedure and anesthesia) on release of $^{125}$I from the thyroid gland. Once the saline control or designated dose of TRH or TRH analogue has been injected, blood samples (0.2 ml) are collected from the tail vein of each rat at 30 minutes, 1 hr, 2 hrs, and 3 hrs. and the $^{125}$I content evaluated as described above. Upon completion of the experiment, animals are kept for a 24 hr time period to observe any adverse toxicological effects. If they maintain their usual behavior (vital signs), it is assumed the compounds tested cause no overt physiological effects.

An increase in I-125 content above the basal level, as exemplified by the saline control, indicates a TRH induced release of TSH (thyrotropin stimulating hormone) which in turn causes release of I-125 from the thyroid. This type of response means the TRH-TRH-thyroid hormone physiologic mechanism (hypothalamo-pituitary-thyroid axis) is working properly, and the animals are suitable for testing. The animals are then challenged, using the technique described above, with various doses of TRH and observed for a dose-related response. For a given time period (such as ½ hr, 1 hr, 2 hrs) that the blood sample is collected following injection of TRH or TRH analogue, a graded response when increasing doses are injected should be noted. For each dose level considered, the radio-activity content of I-125 (cpm) per 200 μl of blood is evaluated at each time period and subtracted from the saline control radioactivity (I-125) content to obtain the Δ cpm released from thyroid. The net cpm released is therefore evaluated, rather than the absolute radio-activity for each time period and dose level.

| Example | | (I-125) cpm/200 ul blood at THR | Δ cpm |
|---|---|---|---|
| | saline | 120 | 0 |
| | 0.4 μgm TRH | 261 | +141 |
| | 4 μgm TRH | 358 | +238 |

To evaluate the effect of TRH analogues (TRH-CMK or TRH-DMK) on the TRH-TSH release of I-125 from the thyroid, each animal of a test group (4 animals) was injected with 1 ml of a given dose of the TRH analogue into the tail vein. One-half later, 0.2 ml of blood was collected from the tail vein and at the same time 1 ml of a given dose TRH was injected. Blood samples (0.2 ml) were then collected at various times (e.g. ½, 1 hr, 2 hrs, etc.) and evaluated for their I-125 content. In essence, the data estabilishes (a) a dose-response curve for TRH given alone; and (b) a dose-response curve for an animal challenged with the TRH-analogue; with observation of significant changes in the curves over time.

| Example | (a) TRH: | | | | |
|---|---|---|---|---|---|
| | | cpm/0.2 ml at 0 time | ½ hr | 1 hr | 2 hr |
| | | Δ cpm: | " | " | " |
| | (b) TRH-analogue given collect blood sample (0.2 ml) (control sample) wait ½ hr, then give TRH | | | | |

-continued

| Collect blood sample at: | | | |
|---|---|---|---|
| cpm/0.2 ml: | ½ hr | 1 hr | 2 hr |
| Δ cpm/0.2 ml: | " | " | " |

VII. Method of Preparation of the Chloromethylketones of Enkephalins

A. t-Boc-Amino Acids were prepared by one of the following methods.

(1) t-Boc-Azide Method t-Boc-Azidoformate was prepared from t-butyl carbazate according to the method of L. A. Carpino et al *J. Am. Chem. Soc.* 82, 2725 (1960) except that the final distillation was done at 40 degrees C. (3 mm Hg) rather than 90–95 degrees C. (140 mm Hg).

t-Butyl Azidoformate was then used to prepare t-Boc-Amino Acids according to the method of (1) E. Schnabel *Ann. Chem.* 702 188 (1967) or (2) Z. Grzonka *Synthesis* pg. 661 (1974).

(2) BOC-ON (Aldrich)

2-t-butoxycarbonyloxyimino-2-phenyl acetonitrile method.

t-Boc-Amino Acids were prepared using this reagent according to the method of M. Itoh, *Tetrahedron Letters*, 4393 (1975).

(3) Di-tert.-butyldicarbonate Method t-BOC-Amino Acids were prepared according to the method of L. Moroder et al *Hoppe-Seyler's Z. Physiol. Chem.* 357 1651 (1976).

B. Attachment of t-Boc-L-Leucine to a chloromethylated polystyrene resin. Chloromethyl-copoly (styrene-1% divinyl benzene) 200–400 mesh (Bio-Rad, 5 g., 5.95 mmol of Cl) was suspended in 35 ml purified DMF and placed in a 50 degree C. oil bath. t-Boc-L-Leucine (1.10 grams, 4.75 mmoles) and cesium carbonate (0.75 g, 2.38 mmol) were suspended in 5 ml of purified DMF and added to the resin. After mixing with an overhead stirrer for 18–24 h at 50 degrees C. the resin was filtered and washed 3× each with DMF, DMF-H$_2$O (9:1), DMF and CH$_2$Cl$_2$ and then dried. The t-Boc-L-leucine resin contained between 0.25–0.40 mmole Leucine/g resin.

C. Preparation of L-Leucine-Resin-HCl 5 grams t-Boc-L-Leucine-Resin from B was placed in a Solid Phase Peptide Synthesis (SPPS) reaction chamber and washed 3× with CH$_2$Cl$_2$ and purified Dioxane*. This was followed with a 20 ml prewash of 4.25 N HCl/Dioxane solution and then 30 minutes of shaking with a 4.25 N HCl/Dioxane. After the 30 minutes the resin was rinsed 3× with purified Dioxane*, CH$_2$Cl$_2$ and CHCl$_3$.

*dioxane: In all cases the dioxane was purified before use according to method (a) of Fieser and Fieser *Reagents for Organic Synthesis* (1967) pg. 333.

D. L-Leucine-Resin

The L-Leucine-Resin-HCl was then washed with 20 ml 10% Diisopropylethylamine (DIEA) CHCl$_3$ and then shaken for 10 min. with 30 ml 10% DIEA-CHCl$_3$. After the 10 minutes the resin was washed 3× each with CHCl$_3$, and CH$_2$Cl$_2$.

E. Preparation of t-Boc-L-Phenylalanine-L-Leucine-Resin 0.995 grams t-Boc-L-Phenylalanine (3.75 mmol) was dissolved in a minimum amount (about 5 ml) CH$_2$Cl$_2$ and added to the resin from D. After shaking for 10 minutes 0.774 g (3.75 mmol) Dicyclohexylcarbodiimide which had previously been dissolved in 10–15 ml CH$_2$Cl$_2$ was added to the resin. After shaking for 2 hours a small sample of the resin was removed and the extent of the coupling reaction checked with ninhydrin according to the method of E. Kaiser *Anal. Biochem.* 34 595 (1970). If the resin sample proved to be ninhydrin-negative the sequence of steps was repeated beginning with (C) and continuing to (E) where now the next amino acid [t-Boc-Glycine] would be substituted for t-Boc-L-Phenylalanine. In this manner t-Boc-Glycine, t-Boc-D-Alanine and t-Boc-L-Tyrosine were sequentially coupled to the L-Phenylalanine-L-Leucine-Resin. If the sample was ninhydrin-positive, the reaction was washed 3× each with CH$_2$Cl, 10% AcOH EtOH, CH$_2$Cl$_2$, CHCl$_3$ and the sequence repeated at Step (D).

F. Transesterification of Resin Bound Peptide

The completed pentapeptide t-Boc-L-Tyrosine-D-Ala-Gly-Phe-Leu-Resin was then removed from the reaction chamber and placed in a 250 ml RB flask to which was then added 180 ml anhydrous MeOH and 8 ml Et$_3$N. The mixture was stirred at room temperature for about 25 hours, filtered, and the filtrate evaporated to dryness under N$_2$ to yield about 1.8 grams of a yellow product.

G. Saponification of t-Boc-D-Ala$^2$-Leucine Enkephalin

To the yellow product obtained in (F) was added 0.66 gram NaOH in 120 ml anhydrous MeOH. The solution was stirred at room temperature for 1 hour, then neutralized to pH 7.5 with dilute HCl, and evaporated to dryness under N$_2$. The solid residue was then thoroughly suspended in absolute MeOH (about 25 ml), filtered, then evaporated again to dryness.

H. Purification of t-Boc-D-Ala$^2$-Leucine Enkephalin

The crude saponified material from (G) was purified by (1) Gel filtration of Sephadex G-10 (0.2 N AcOH) (2) Partition chromatography according to PORATH et al. *Nature* 201 76 (1964) using Butanol:Pyridine-Benzene:0.1% AcOH (60:10:20:90) and then finally (3) Gel filtration again on Sephadex G-10 (0.2 N AcOH). The pure t-Boc-D-Ala$^2$-Leucine Enkephalin was obtained as a white powder.

Analysis: A small sample was removed and de-protected with trifluoroacetic acid (30 minutes):

| TLC [single spot, all systems] | Rf |
|---|---|
| EtOAc: Pyridine: HOAc: H$_2$O (50:50:10:30) | 0.87 |
| n-Butanol: HOAc: H$_2$O (4:1:1) | 0.62 |
| n-Butanol: HOAc: H$_2$O (4:1:5) | 0.70 |
| n-Butanol: HOAc: H$_2$O: Pyridine (60:12:48:40) | 0.70 |

Amino Acid Analysis
Gly=1.02
Ala=1.00
Tyr=1.05
Phe=1.02 [Leucine not available]

The IR showed strong absorption bands representing the carbonyl stretch for amides (1655 cm$^{-1}$) and for free acid (1705 cm$^{-1}$).

I. Preparation of t-Boc-D-Ala$^2$-Leucine Enkephalin Diazomethylketone 1.15 mmol (840 mg) t-Boc-D-Ala$^2$-Leucine Enkephalin Acetate salt was dissolved in anhydrous THF and with continuous stirring the temperature lowered to −15 degrees C. in an ice/salt bath. The entire reaction was carried out under nitrogen atmosphere. To this solution was added 1.15 mmol (0.2 ml, 159 mg) Triethylamine and, two minutes later, 1.15 mmol (0.15 ml, 0.16 mg) isobutyl chloroformate. After 2–5 minutes the solution was filtered into a 50 ml RB Flask containing about 20 ml of about 0.4 M Diazomethane at −15 degrees C. The diazomethane was freshly prepared from N-methyl-N-nitroso-p-toluenesulfonamide. The solution was stirred overnight and gradually allowed to come to room temperature. Solvent was removed under a stream of nitrogen.

The IR shows a characteristic sharp band at 2105 cm$^{-1}$ for the diazo group.

J. Preparation of D-Ala$^2$-Leucine Enkephalin Chloromethylketone

To the crude t-Boc-D-Ala$^2$-Leucine Enkephalin diazomethylketone was added about 10 ml 4.25 N HCl/Dioxane and the solution allowed to sit at room temperature for 30–45 minutes. The HCl/Dioxane was then removed under a stream of dry nitrogen. The yellow/brown residue was then recrystallized from CH$_2$Cl$_2$/Et$_2$O to yield a cream colored precipitate.

TLC (thin lager chromatography) single spot
n-Butanol:HOAc:H$_2$O:Pyridine (60:12:48:40)
Rf=0.77, IR spectra shows a shift in the carbonyl band from 1705 cm$^{-1}$ (free acid) to 1735 cm$^{-1}$, typical of chloromethylketones.

6 Point Parallel Line Assay Design:
   3 sample, 3 standard samples
   2 animals per dose level
   Responses expressed in (Ng/ml)
Animals challenged with peptide derivative dissolved in 0.85% NaCl.
Total Injection Volume: 0.25 ml
Anatomical Site of Injection: Jugular vein Samples obtained by subjecting animal to ether anesthesia, and sacrificing animal.

Each animal was injected via jugular vein 0.25 ml of peptide derivative: to insure sample was injected into vein, the syringe plunger was gently retracted, if blood could be withdrawn, then the sample was injected. Following injection, the syringe was rinsed with blood and injected. ½-hour following injection of the peptide derivative, using the same procedure, a TRH dose-response curve was made using the same injection technique.

Schedule
  0 time—injection of TRH derivative (80 ugm)
  ½ hr.—injection of TRH (4, 40, and 80 ugm)
  1 hrs.—blood sample collected
2 animals/dose level

| Inhibitor | Serum TSH level ng/ml Dose of TRH given | | | |
|---|---|---|---|---|
| (80 gm in 0.25. ml) | 0 µg | 4 µg | 40 µg | 80 µg |
| FIRST EXPERIMENT | | | | |
| None (saline injected) | 121 | 312 | 412 | 1139 |
| pGluHisPro—CH$_2$Cl | | 312 | 512 | 1216 |
| pGluHisPro—CHN$_2$ | | 305 | 200 | 566 |
| pGlu(ImN$^{3Me}$)HisPro—CH$_2$Cl | | 91 | 81 | 200 |
| pGlu(ImN$^{3Me}$)HisPro—CHN$_2$ | | 61 | 89 | 309 |
| SECOND EXPERIMENT | | | | |
| None (saline injected) | 106 | 167 | 612 | 839 |
| pGluHisPro—CH$_2$Cl | | 169 | 616 | 918 |
| pGluHisPro—CHN$_2$ | | 305 | 200 | 566 |
| pGlu(Imn$^{3Me}$)HisPro—CH$_2$Cl | | 115 | 207 | 600 |
| pGlu(ImN$^{3Me}$)HisPro—CHN$_2$ | | 95 | 41 | 65 |

| Inhibitor | Serum Prolactin Level ng/ml Dose of TRH Given | | | |
|---|---|---|---|---|
| (80 µg in 0.25 ml) | 0 µg | 4 µg | 40 µg | 80 µg |

| -continued | | | | |
|---|---|---|---|---|
| FIRST EXPERIMENT | | | | |
| None (saline injected) | 49 | 61 | 76 | 216 |
| GluHisPro—CH$_2$Cl | | 84 | 20 | 21 |
| pGluHisPro—CHN$_2$ | | 27 | 65 | 31 |
| pGlu(ImN$^{3Me}$)HisPro—CH$_2$Cl | | 65 | 77 | 135 |
| pGlu(ImN$^{3Me}$)HisPro—CHN$_2$ | | 20 | 16 | 3 |
| SECOND EXPERIMENT | | | | |
| None (saline injected) | 36 | 46 | 150 | 181 |
| pGluHisPro—CH$_2$Cl | | 32 | 75 | 168 |
| pGluHisPro—CHN$_2$ | | 39 | 56 | 108 |
| pGlu(ImN$^{3Me}$)HisPro—CH$_2$Cl | | 19 | 40 | 43 |
| pGlu(ImN$^{3Me}$)HisPro—CHN$_2$ | | 16 | 46 | 75 |

Although this invention has been described with reference to illustrative embodiments thereof, it will be apparent to those skilled in the art that the principles of this invention can be embodied in other forms within the scope of the following claims.

What is claimed is:

1. A biologically active derivative of a precursor carboxyl-terminal polypeptide comprising a sequence of α-amino acid residues terminated at one end thereof with a terminal carboxyl group and at the other end thereof with a terminal amino group, said precursor polypeptide being selected from the group consisting of the free acid forms of (a) polypeptide hypothalamic releasing factors, (b) polypeptide hypothalamic inhibitory factors, (c) polypeptide enkephalins, and (d) polypeptide fragments thereof each consisting of a biologically-active polypeptide segment of one of said precursor polypeptides, said derivative comprising said precursor polypeptide wherein the hydroxyl group of the terminal carboxyl group is replaced by —CH—N$_2$ or —CH$_2$X, wherein X is Cl, Br, or I.

2. The invention of claim 1, wherein the derivative is of the formula

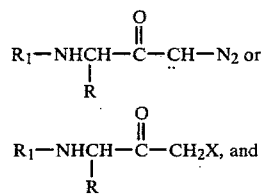

(a) R is Pro side chain and R$_1$ is pyroGlu-His;
(b) R is Met or Leu side chains and R$_1$ is Tyr-Gly-Gly-Phe; or
(c) R is H and R$_1$ is pyroGlu-His-Trp-Ser-Tyr-Gly-Leu-Arg-Pro.

3. The invention of claim 1, wherein each of the α-amino acid residues in the polypeptide includes a side chain consisting of (a) a natural side chain, or (b) an unnatural side chain having, other than hydrogen, the same number of atoms as, one more atom than, or one less atom than, the natural side chain, thus forming an unnatural α-amino acid residue not naturally occurring at that position in the sequence.

4. The invention of claim 3, wherein the derivative is of the formula

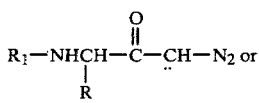

(a) R is Met or Leu side chain and R$_1$ is Tyr-Ala-Gly-Phe;
or (b) R is Met or Leu side chain and R$_1$ is Tyr-Gly-Ala-Phe.

5. The invention of claim 3, wherein at least one of the α-amino acid residues is replaced with its stereoisomer.

6. The invention of claim 5, wherein the derivative is of the formula

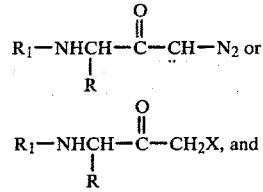

R is Met or Leu side chain and R$_1$ is Tyr-D-Ala-Gly-Phe.

7. The invention of claim 3 or 5 wherein at least one of the α-amino acid residues is methylated, ethylated, or allylated.

8. The invention of claim 3 or 5 wherein the derivative is of the formula

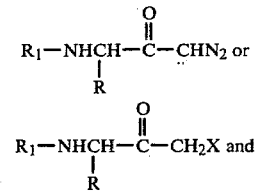

R is Pro side chain and R$_1$ is pyroGlu-N-methylHis or PyroGlu-N-ethylHis.

9. The invention of claims 3, 5 or 7, wherein at least one of the α-amino acid residues of the precursor polypeptide includes a side chain having a ring structure and said derivative includes a corresponding α-amino acid having a side chain wherein the ring structure has one more or one less atom than does the original ring structure and/or at least one of the original ring atoms is replaced with an atom of a different element.

10. The invention of claims 3, 5 or 7, wherein the derivative is of the formula

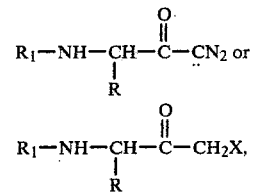

R is Pro side chain and R$_1$ is pyroGlu-Phe.

11. The invention of claim 1, wherein said fragment is a hypothalamic releasing or inhibitory factor or an enkephalin polypeptide wherein the carboxyl-terminal α-amino acid residue is deleted so that the penultimate α-amino acid residue of the hypothalamic or enkephalin polypeptide sequence provides the terminal carboxyl group of the polypeptide fragment.

12. The invention of claim 11, wherein the derivative is of the formula

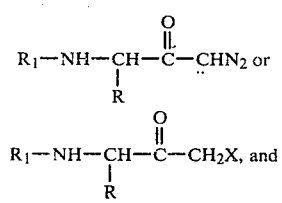

(a) R is His side chain and $R_1$ is pyroGlu, or
(b) R is Pro side chain and $R_1$ is pyroGlu-His-Trp-Ser-Tyr-D-Ala-Leu-Arg.

13. The invention of claim 11 wherein at least one of the α-amino residues of the precursor polypeptide fragment includes a side chain having a ring structure and said derivative includes a corresponding α-amino acid having a side chain wherein the ring structure has one more or one less atom than does the original ring structure and/or at least one of the original ring atoms is replaced by an atom of a different element.

14. The invention of claim 13 wherein the derivative is of the formula

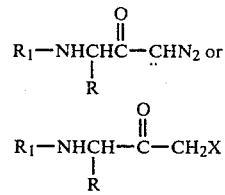

wherein R is Phe side chain when $R_1$ is pyroGlu; or R is His side chain when $R_1$ is cyclopentoyl.

* * * * *